US009545309B2

United States Patent
Alkhatib et al.

(10) Patent No.: US 9,545,309 B2
(45) Date of Patent: *Jan. 17, 2017

(54) REPOSITIONING OF PROSTHETIC HEART VALVE AND DEPLOYMENT

(71) Applicant: St. Jude Medical, Cardiology Division, Inc., St. Paul, MN (US)

(72) Inventors: Yousef F. Alkhatib, Edina, MN (US); Peter N. Braido, Wyoming, MN (US)

(73) Assignee: St. Jude Medical, Cardiology Divisions, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/944,920

(22) Filed: Nov. 18, 2015

(65) Prior Publication Data

US 2016/0067041 A1    Mar. 10, 2016

Related U.S. Application Data

(63) Continuation of application No. 14/689,212, filed on Apr. 17, 2015, which is a continuation of application
(Continued)

(51) Int. Cl.
*A61F 2/24* (2006.01)
*A61F 2/95* (2013.01)

(52) U.S. Cl.
CPC ............ *A61F 2/2436* (2013.01); *A61F 2/243* (2013.01); *A61F 2/2409* (2013.01);
(Continued)

(58) Field of Classification Search
CPC .... A61F 2/2412; A61F 2/2418; A61F 2/2427; A61F 2/243; A61F 2/2436; A61F 2002/9534; A61F 2220/0075
See application file for complete search history.

(56) References Cited

U.S. PATENT DOCUMENTS 3,657,744 A    4/1972    Ersek
4,275,469 A    6/1981    Gabbay
(Continued)

FOREIGN PATENT DOCUMENTS

AU    2011202175 B1    7/2011
DE    19857887 A1    7/2000
(Continued)

OTHER PUBLICATIONS

Christoph H. Huber, et al., "Direct-Access Valve Replacement", Journal of the American College of Cardiology, vol. 46, No. 2, pp. 366-370, (Jul. 19, 2005).
(Continued)

*Primary Examiner* — Robert Lynch

(57) ABSTRACT

A collapsible prosthetic heart valve includes a stent and a valve assembly. The stent has an annulus section with a relatively small cross-section, and an aortic section with a relatively large cross-section. The valve assembly, including a cuff and a plurality of leaflets, is secured to the stent in the annulus section such that the valve assembly can be entirely deployed in the native valve annulus and function as intended while at least a portion of the aortic section is held by the delivery device in a manner that allows for resheathing. The configuration of the prosthetic valve is such that the valve leaflets can fully coapt and the valve can function properly even when the stent and/or valve assembly become distorted upon deployment or use.

26 Claims, 17 Drawing Sheets

Related U.S. Application Data

No. 13/215,901, filed on Aug. 23, 2011, now Pat. No. 9,039,759.

(60) Provisional application No. 61/438,451, filed on Feb. 1, 2011.

(52) U.S. Cl.
CPC .......... *A61F 2/2418* (2013.01); *A61F 2/2412* (2013.01); *A61F 2/2427* (2013.01); *A61F 2002/9517* (2013.01); *A61F 2002/9534* (2013.01); *A61F 2220/005* (2013.01); *A61F 2220/0066* (2013.01); *A61F 2220/0075* (2013.01); *A61F 2230/008* (2013.01); *A61F 2230/0013* (2013.01); *A61F 2230/0054* (2013.01); *A61F 2250/0039* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,922,905 A | 5/1990 | Strecker |
| 5,078,720 A | 1/1992 | Burton et al. |
| 5,391,172 A | 2/1995 | Williams et al. |
| 5,411,552 A | 5/1995 | Andersen et al. |
| 5,415,664 A | 5/1995 | Pinchuk |
| 5,456,667 A | 10/1995 | Ham et al. |
| 5,480,423 A | 1/1996 | Ravenscroft et al. |
| 5,484,444 A | 1/1996 | Braunschweiler et al. |
| 5,702,418 A | 12/1997 | Ravenscroft |
| 5,824,041 A | 10/1998 | Lenker et al. |
| 5,843,167 A | 12/1998 | Dwyer et al. |
| 5,935,163 A | 8/1999 | Gabbay |
| 5,961,549 A | 10/1999 | Nguyen et al. |
| 5,980,533 A | 11/1999 | Holman |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,269,819 B1 | 8/2001 | Oz et al. |
| 6,368,348 B1 | 4/2002 | Gabbay |
| 6,391,050 B1 | 5/2002 | Broome |
| 6,419,695 B1 | 7/2002 | Gabbay |
| 6,458,153 B1 | 10/2002 | Bailey et al. |
| 6,468,299 B2 | 10/2002 | Stack et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,736,845 B2 | 5/2004 | Marquez et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,329,278 B2 | 2/2008 | Seguin et al. |
| 7,374,573 B2 | 5/2008 | Gabbay |
| 7,381,218 B2 | 6/2008 | Schreck |
| 7,399,315 B2 | 7/2008 | Iobbi |
| 7,452,371 B2 | 11/2008 | Pavcnik et al. |
| 7,476,244 B2 | 1/2009 | Buzzard et al. |
| 7,510,572 B2 | 3/2009 | Gabbay |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,313,525 B2 | 11/2012 | Tuval et al. |
| 8,353,955 B2 | 1/2013 | Styrc et al. |
| 8,568,475 B2 | 10/2013 | Nguyen et al. |
| 8,679,174 B2 | 3/2014 | Ottma et al. |
| 2002/0036220 A1 | 3/2002 | Gabbay |
| 2002/0045936 A1* | 4/2002 | Moe .................... A61F 2/2412 623/2.17 |
| 2002/0183827 A1 | 12/2002 | Derus et al. |
| 2003/0040792 A1 | 2/2003 | Gabbay |
| 2003/0050694 A1 | 3/2003 | Yang et al. |
| 2003/0130726 A1 | 7/2003 | Thorpe et al. |
| 2003/0144725 A1 | 7/2003 | Lombardi |
| 2004/0039436 A1 | 2/2004 | Spenser et al. |
| 2004/0049262 A1 | 3/2004 | Obermiller et al. |
| 2004/0093060 A1 | 5/2004 | Seguin et al. |
| 2004/0093075 A1 | 5/2004 | Kuehne |
| 2004/0148009 A1 | 7/2004 | Buzzard et al. |
| 2004/0186563 A1 | 9/2004 | Lobbi |
| 2004/0210304 A1 | 10/2004 | Seguin et al. |
| 2004/0260390 A1 | 12/2004 | Sarac et al. |
| 2005/0004583 A1 | 1/2005 | Oz et al. |
| 2005/0049667 A1 | 3/2005 | Arbefeuille et al. |
| 2005/0096726 A1 | 5/2005 | Sequin et al. |
| 2005/0137688 A1 | 6/2005 | Salahieh et al. |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0025857 A1 | 2/2006 | Bergheim et al. |
| 2006/0074484 A1 | 4/2006 | Huber |
| 2006/0122692 A1 | 6/2006 | Gilad et al. |
| 2006/0173532 A1 | 8/2006 | Flagle et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0282150 A1 | 12/2006 | Olson et al. |
| 2006/0282157 A1 | 12/2006 | Hill et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0156225 A1 | 7/2007 | George et al. |
| 2007/0213813 A1 | 9/2007 | Von Segesser et al. |
| 2007/0244545 A1 | 10/2007 | Birdsall et al. |
| 2007/0244552 A1 | 10/2007 | Salahieh et al. |
| 2007/0260301 A1 | 11/2007 | Chuter et al. |
| 2007/0288087 A1 | 12/2007 | Fearnot et al. |
| 2008/0004688 A1 | 1/2008 | Spenser et al. |
| 2008/0004696 A1 | 1/2008 | Vesely |

(56) References Cited

U.S. PATENT DOCUMENTS

| | | |
|---|---|---|
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0157175 A1 | 6/2009 | Benichou |
| 2009/0240320 A1 | 9/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 | 5/2010 | Paul et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0282425 A1 | 11/2011 | Dwork |
| 2012/0197391 A1 | 8/2012 | Alkhatib et al. |
| 2013/0079869 A1 | 3/2013 | Straubinger et al. |

FOREIGN PATENT DOCUMENTS

| | | |
|---|---|---|
| DE | 20000659 U1 | 5/2001 |
| DE | 10121210 A1 | 11/2002 |
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| JP | 2010523234 | 7/2010 |
| JP | 2010528761 A | 8/2010 |
| JP | 2010540079 A | 12/2010 |
| JP | 2011512922 | 4/2011 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0069368 A2 | 11/2000 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 02/067782 A2 | 9/2002 |
| WO | 03047468 A1 | 6/2003 |
| WO | 2005070343 A1 | 8/2005 |
| WO | 2006073626 A2 | 7/2006 |
| WO | 2007071436 A2 | 6/2007 |
| WO | 2008042266 A2 | 4/2008 |
| WO | 2008070797 A2 | 6/2008 |
| WO | 2008125153 A1 | 10/2008 |
| WO | 2008138584 A1 | 11/2008 |
| WO | 2008150529 A1 | 12/2008 |
| WO | 2009029199 A1 | 3/2009 |
| WO | 2009042196 A2 | 4/2009 |
| WO | WO 2009061389 A2 * | 5/2009 ............ A61F 2/2418 |
| WO | 2009091509 A1 | 7/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012026965 A2 | 3/2012 |
| WO | 2012036741 A2 | 3/2012 |

OTHER PUBLICATIONS

John G. Webb et al., "Percutaneous Aortic Valve Implantation Retrograde From the Femoral Artery", Circulation, 2006; 113:842-850 (Feb. 6, 2006).

M. J. Mack, "Minimally invasive cardiac surgery", Surgical Endoscopy, 2006, 20:S488-S492, DOI: 10.1007/s00464-006-0110-8 (presented Apr. 24, 2006).

Samuel V. Lichtenstein et al., "Transapical Transcatheter Aortic Valve Implantation in Humans", Circulation. 2006; 114: 591-596 (Jul. 31, 2006).

Samuel V. Lichtenstein, "Closed heart surgery: Back to the future", The Journal of Thoracic and Cardiovascular Surgery, vol. 131, No. 5, pp. 941-943, May 2006.

Textbook "Transcatheter Valve Repair", 2006, pp. 165-186.

Todd M. Dewey et al., "Transapical aortic valve implantation: an animal feasibility study"; The annals of thoracic surgery 2006; 82: 110-116 (Feb. 13, 2006).

Walther et al., "Transapical approach for sutureless stent-fixed aortic valve implantation: experimental results"; European Journal of Cardio-thoracic Surgery 29 (2006) 703-708 (Jan. 30, 2006).

Australian Examination Report for Application No. 2011293898 dated Jul. 26, 2013.

Commonly owned co-pending U.S. Appl. No. 13/212,442, filed Aug. 18, 2011.

Commonly owned co-pending U.S. Appl. No. 13/216,124, filed Aug. 23, 2011.

Commonly owned co-pending U.S. Appl. No. 13/234,782, filed Sep. 16, 2011.

Commonly owned co-pending U.S. Appl. No. 13/788,820, filed Mar. 7, 2013.

International Search Report and Written Opinion for Application No. PCT/US2011/001615 dated Jul. 11, 2012.

International Search Report and Written Opinion for Application No. PCT/US2013/039407 dated Feb. 10, 2014.

International Search Report Application No. PCT/US2011/048963, dated Dec. 15, 2011.

International Search Report Application No. PCT/US2011/048967, dated Dec. 15, 2011.

International Search Report Application No. PCT/US2011/048989, dated Dec. 15, 2011.

International Search Report for Application No. PCT/US2011/001450 dated Mar. 5, 2012.

International Search Report for Application No. PCT/US2011/001597 dated Mar. 7, 2012.

Overview of PRE-CE Mark Transcatheter Aortic Valve Technologies (powerpoint—dated Jun. 1, 2010).

* cited by examiner

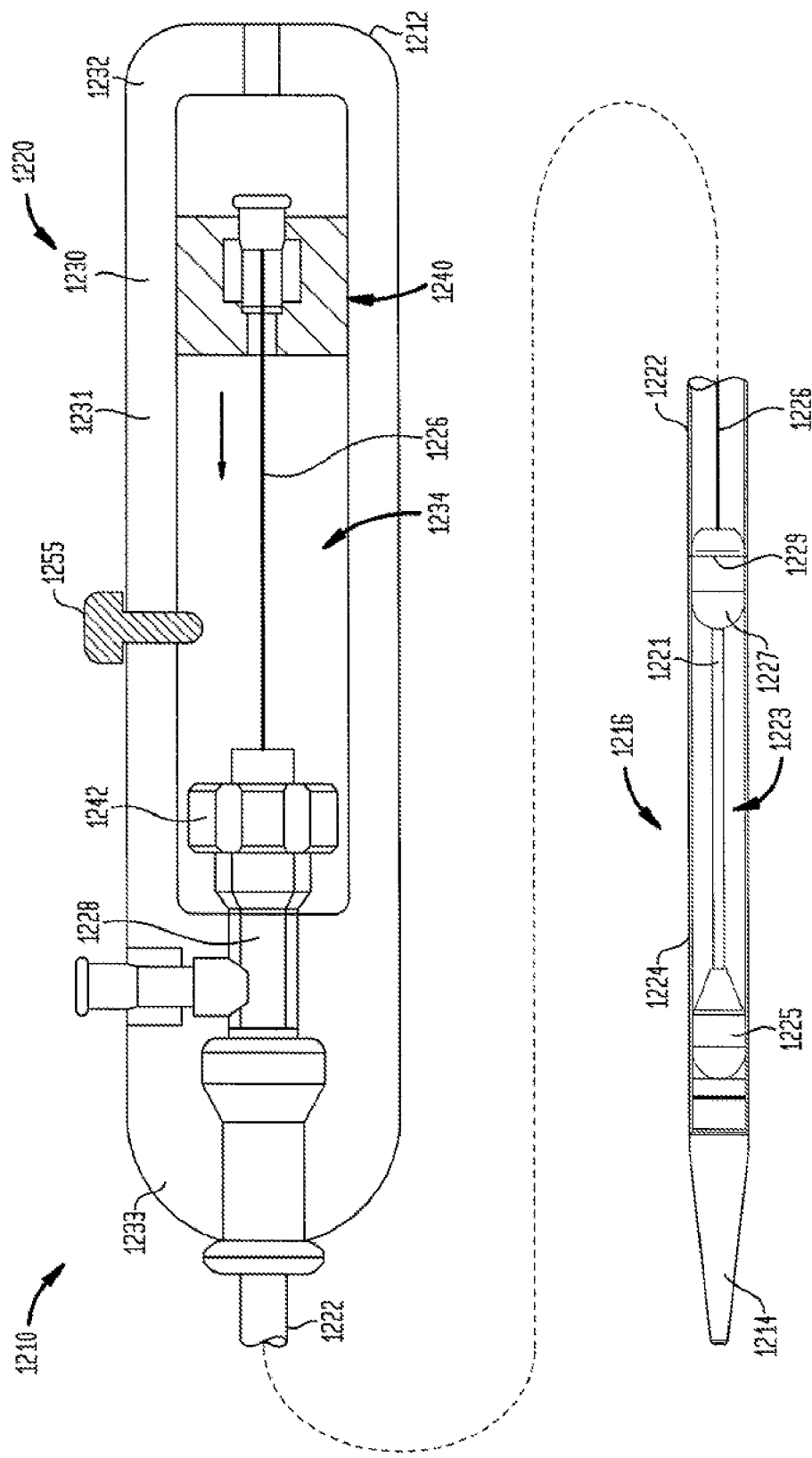

REPOSITIONING OF PROSTHETIC HEART VALVE AND DEPLOYMENT

CROSS-REFERENCE TO RELATED APPLICATIONS

This application is a continuation of U.S. patent application Ser. No. 14/689,212, filed Apr. 17, 2015, which is a continuation of U.S. patent application Ser. No. 13/215,901 filed Aug. 23, 2011, which claims the benefit of the filing date of U.S. Provisional Patent Application No. 61/438,451 filed Feb. 1, 2011, the disclosures of which are hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves that may be repositioned during the deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheaths the annulus end of the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. In order for the user to be able to more readily resheath a valve, it is preferable that the valve be only partially deployed, with a portion of the valve still collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheath and reposition the valve. Moreover, it is not possible at this time to determine whether a valve assembly will function as intended without full deployment of the heart valve. Due to anatomical variations between patients, a fully deployed heart valve may need to be removed from the patient if it appears that the valve is not functioning properly. Removing a fully deployed heart valve increases the length of the procedure and increases the risk of infection and/or damage to heart tissue.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

SUMMARY OF THE INVENTION

One aspect of the disclosure provides a prosthetic heart valve including a collapsible and expandable stent having a proximal end, a distal end, an annulus section adjacent the proximal end and an aortic section adjacent the distal end. The annulus section has a first expanded cross-section and the aortic section has a second expanded cross-section larger than the first expanded cross-section. A plurality of commissure points are disposed in the annulus section. A collapsible and expandable valve assembly is disposed entirely within the annulus section between the proximal end of the stent and the plurality of commissure points. The valve assembly includes a plurality of leaflets connected to the plurality of commissure points. The plurality of commissure points are spaced from the distal end of the stent by a selected distance such that the prosthetic valve can be partially deployed from a delivery device at a target site by withdrawing a portion of the sheath of the delivery device from around the prosthetic valve, and the valve assembly can function as intended while the distal end of the stent is held within the sheath of the delivery device in a manner that enables resheathing.

In one example, a plurality of commissure points are spaced at a selected distance of about two-thirds of the length of the stent from the proximal end to the distal end. In another example, the plurality of leaflets have an open condition in which the leaflets are spaced apart from one another to define a flow passageway through the stent, and a closed condition in which the leaflets coapt to occlude the flow passageway, the leaflets being disposed completely within the annulus section in both the open and closed conditions. In another example, the valve assembly further includes a cuff disposed in the annulus section. In yet another example, the cuff is disposed on a lumenal surface of the annulus section. Alternatively, the cuff is disposed on an ablumenal surface of the annulus section. The plurality of leaflets may include two or three leaflets.

In another aspect, the prosthetic heart valve includes a collapsible and expandable stent having a proximal end, a distal end, an annulus section adjacent the proximal end, an aortic section adjacent the distal end, and a transition section between the aortic section and the annulus section. The annulus section has a first expanded cross-section, and the aortic section has a second expanded cross-section larger than the first expanded cross-section. The transition section has an expanded cross-section which transitions from the first expanded cross-section to the second expanded cross-section. A plurality of commissure points is disposed at a juncture between the annulus section and the transition section. A collapsible and expandable valve assembly is disposed entirely within the annulus section between the proximal end of the stent and the plurality of commissure points, the valve assembly including a plurality of leaflets connected to the plurality of commissure points. The plurality of commissure points are spaced from the distal end of the stent by a selected distance such that the prosthetic valve can be partially deployed from a delivery device at a target site by withdrawing a portion of the sheath of the delivery device from around the prosthetic valve, and the valve assembly can function as intended while the distal end of the stent is held within the sheath of the delivery device in a manner that enables resheathing.

In another aspect, a prosthetic heart valve includes a collapsible and expandable stent having a proximal end, a distal end, an annulus section adjacent the proximal end and an aortic section adjacent the distal end. The annulus section has a first expanded cross-section and an unconstrained shape and the aortic section has a second expanded cross-section larger than the first expanded cross-section. A plurality of commissure points are disposed in the annulus section. A collapsible and expandable valve assembly is disposed entirely within the annulus section between the proximal end of the stent and the plurality of commissure points. The valve assembly includes a plurality of leaflets connected to the plurality of commissure points, the plurality of leaflets having an open condition in which the leaflets are spread apart from one another to define a flow passageway through the stent, and a closed condition in which the leaflets form coaptation sections to occlude the flow passageway. The coaptation sections occlude the flow passageway both when the annulus section has the unconstrained shape and when the annulus section is distorted from the unconstrained shape.

In one example, the coaptation sections are oriented substantially parallel to a longitudinal axis of the stent in the closed condition. In another example, each coaptation section has a length in a direction from a free-edge of a leaflet toward the stent, the length being between about 1 mm and about 5 mm. In another example, each of the plurality of leaflets forms a belly contour before converging at the coaptation section in the closed condition. In another example, each of the plurality of leaflets forms a flat belly before converging at the coaptation section in the closed condition.

In one aspect the disclosure provides a method of deploying a prosthetic heart valve at a target site. The method includes introducing a delivery device to the target site, the delivery device housing a prosthetic heart valve in a collapsed condition and having an outer sheath surrounding the prosthetic heart valve. The prosthetic heart valve includes a collapsible and expandable stent having a proximal end, a distal end, an annulus section adjacent the proximal end and an aortic section adjacent the distal end. The heart valve further includes a plurality of commissure points disposed in the annulus section and a collapsible and expandable valve assembly disposed entirely within the annulus section between the proximal end of the stent and the plurality of commissure points. The method further includes withdrawing the sheath a first distance to partially deploy the prosthetic heart valve at the target site, the prosthetic heart valve being deployed from the proximal end of the stent toward the distal end of the stent such that the valve assembly is fully deployed at the first distance and can function as intended while the distal end of the stent is held within the sheath of the delivery device. The sheath is fully withdrawn to fully deploy the prosthetic heart valve.

In another aspect the disclosure provides a method of deploying a prosthetic heart valve at a target site. The method includes introducing a delivery device to the target site, the delivery device housing a prosthetic heart valve in a collapsed condition and having an outer sheath surrounding the prosthetic heart valve. The prosthetic heart valve includes a collapsible and expandable stent having a proximal end, a distal end, an annulus section adjacent the proximal end and an aortic section adjacent the distal end, a plurality of commissure points disposed in the annulus section, and a collapsible and expandable valve assembly disposed entirely within the annulus section between the proximal end of the stent and the plurality of commissure points. The method further includes withdrawing the sheath a first distance to partially deploy the prosthetic heart valve at the target site, the prosthetic heart valve being deployed from the proximal end of the stent toward the distal end of the stent such that the valve assembly is fully deployed at the first distance and can function as intended while the distal end of the stent is held within the sheath of the delivery device. The prosthetic heart valve is resheathed and the sheath is withdrawn a first distance to partially deploy the prosthetic heart valve at the target site, the prosthetic heart valve being deployed from the proximal end of the stent toward the distal end of the stent such that the valve assembly is fully deployed at the first distance and can function as intended while the distal end of the stent is held within the sheath of the delivery device.

In one example, the sheath is withdrawn so as to fully deploy the prosthetic heart valve. In another example, the valve assembly includes a plurality of leaflets connected to the plurality of commissure points, the plurality of leaflets having an open condition in which the leaflets are spaced apart from one another to define a flow passageway through the stent, and a closed condition in which the leaflets coapt to occlude the flow passageway and the valve assembly functions as intended by providing adequate coaptation by the leaflets in the closed condition. In another example, partially deploying the prosthetic heart valve includes withdrawing the sheath to uncover only the annulus section of the heart valve and fully deploying the heart valve includes withdrawing the sheath to uncover both the annulus section and the aortic section of the heart valve. In another example, the valve assembly includes a plurality of leaflets connected to the plurality of commissure points, the plurality of leaflets having an open condition in which the leaflets are spaced apart from one another to define a flow passageway through the stent, and a closed condition in which the leaflets coapt to occlude the flow passageway and the plurality of leaflets can fully coapt when the heart valve is partially deployed at the target site. In another example, the plurality of leaflets are capable of forming coaptation sections to occlude the flow passageway, the coaptation sections occluding the flow passageway both when the annulus section has the unconstrained shape and when the annulus section is distorted from the unconstrained shape.

In another aspect, the disclosure provides a method of testing the operability of a prosthetic heart valve at a target site. The method includes introducing a delivery device to the target site, the delivery device housing a prosthetic heart valve in a collapsed condition and having an outer sheath surrounding the prosthetic heart valve. The prosthetic heart valve includes a collapsible and expandable stent having a proximal end, a distal end, an annulus section adjacent the proximal end and an aortic section adjacent the distal end, a plurality of commissure points disposed in the annulus section, and a collapsible and expandable valve assembly disposed entirely within the annulus section between the proximal end of the stent and the plurality of commissure points. The sheath is withdrawn a first distance to partially deploy the prosthetic heart valve at the target site, the prosthetic heart valve being deployed from the proximal end of the stent toward the distal end of the stent such that the valve assembly is fully deployed at the first distance and can function as intended while the distal end of the stent is held within the sheath of the delivery device. Valve function is assessed when the prosthetic heart valve is partially deployed. The prosthetic heart valve can be resheathed.

In one example, introducing the delivery device to the target site includes introducing the delivery device to a target site in vitro. In another example, introducing the delivery device to the target site includes introducing the delivery device to a target site in a mammal. In another example, introducing the delivery device to the target site includes introducing the delivery device to a target site in a human patient.

In another aspect, the disclosure provides a system including a prosthetic heart valve including a collapsible and expandable stent having a proximal end, a distal end, an annulus section adjacent the proximal end and an aortic section adjacent the distal end. The annulus section has a first expanded cross-section and the aortic section has a second expanded cross-section larger than the first expanded cross-section. A plurality of commissure points are disposed in the annulus section, and a collapsible and expandable valve assembly is disposed entirely within the annulus section between the proximal end of the stent and the plurality of commissure points. The valve assembly includes a plurality of leaflets connected to the plurality of commissure points, the plurality of commissure points being spaced from the distal end of the stent by a selected distance such that the prosthetic valve can be partially deployed from a delivery device at a target site by withdrawing a sheath of the delivery device from around the prosthetic valve. The delivery device includes a sheath partially covering the stent and releasably retaining same, wherein the valve assembly is free to operate in a portion of the stent not retained by the sheath.

In another aspect, the disclosure provides a system including a prosthetic heart valve having a collapsible and expandable stent having a proximal end, a distal end, an annulus section adjacent the proximal end and an aortic section adjacent the distal end. The annulus section has a first expanded cross-section and the aortic section has a second expanded cross-section larger than the first expanded cross-section. A plurality of commissure points are disposed in the annulus section, and a collapsible and expandable valve assembly is disposed entirely within the annulus section between the proximal end of the stent and the plurality of commissure points. The valve assembly includes a plurality of leaflets connected to the plurality of commissure points, the plurality of commissure points being spaced from the distal end of the stent by a selected distance such that the prosthetic valve can be partially deployed from a delivery device at a target site by withdrawing a sheath of the delivery device from around the prosthetic valve. The system further includes a delivery device having a sheath capable of being moved from a first configuration in which the sheath partially covers the stent and releasably retains same, wherein the valve assembly is free to operate in a portion of the stent not retained by the sheath, and a second configuration in which the sheath substantially completely covers the stent and the valve assembly is incapable of normal function.

BRIEF DESCRIPTION OF THE DRAWINGS

Various embodiments of the presently disclosed delivery system are disclosed herein with reference to the drawings, wherein:

FIG. 22 is a diagrammatic top plan view of an operating handle for a transapical delivery device for a collapsible prosthetic heart valve, shown with a side elevational view of the distal portion of a transapical catheter assembly.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

Figure 1:
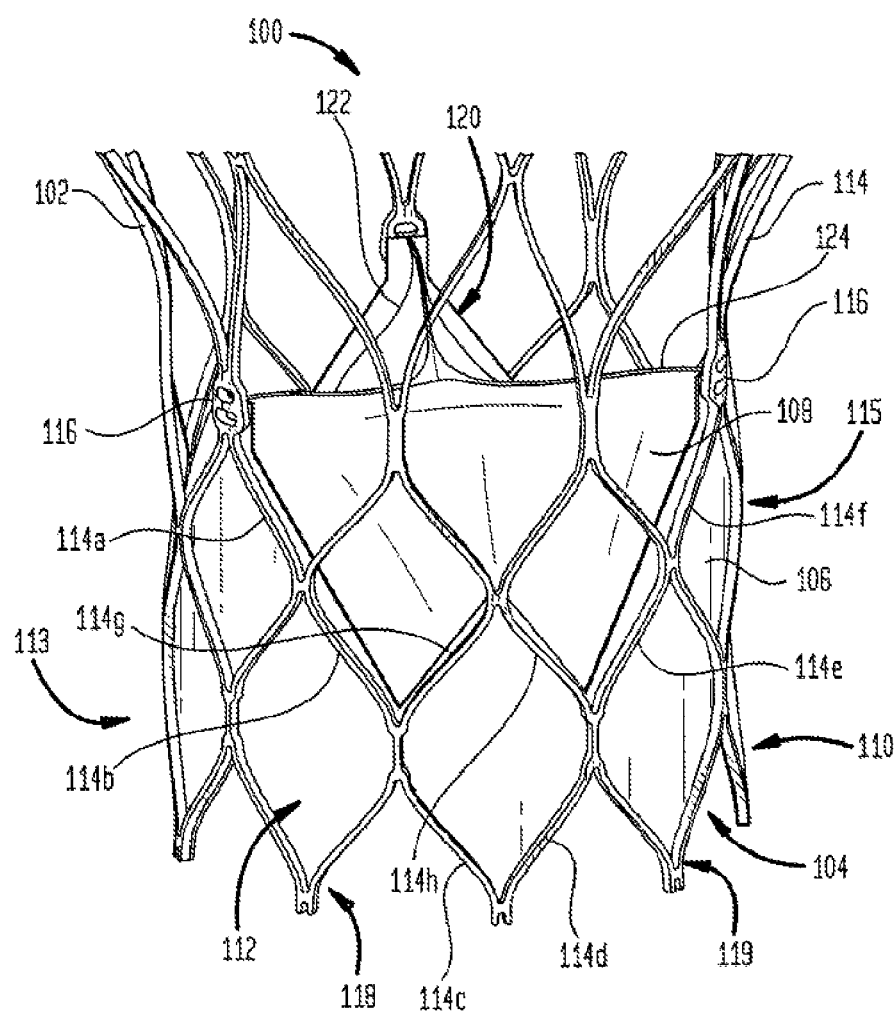
FIG. 1 is a partial side elevational view of a prosthetic heart valve including a valve assembly and a stent.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section (not shown). Each of the annulus section 110 and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure points 116 connecting at least two cells 112 in the longitudinal direction of the stent 102. The commissure points 116 may include eyelets for facilitating the suturing of a valve assembly 104 to the sent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester. In some embodiments, the cuff and/or the sutures may include ultra-high-molecular-weight polyethylene.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the stent 102 by any suitable attachment means, such as suturing, stapling, adhesives or the like. For example, the first edge 122 of each leaflet 108 may be sutured to the stent 102 by passing strings or sutures through the cuff 106 of the valve assembly 104. A second or free edge 124 of each leaflet 108 may coapt with the corresponding free edges of the other leaflets, thereby enabling the leaflets to function collectively as a one-way valve. Thus, the leaflets 108 may be attached to the stent 102 along at least some struts 114 of the stent to enhance the structural integrity of the valve assembly 104.

As shown in FIG. 1, at least one leaflet 108 may be attached to the stent 102 so that its first edge 122 is disposed substantially along specific struts 114a, 114b, 114c, 114d, 114e and 114f located in the annulus section 110 of the stent. That is, the edge 122 is positioned in substantial alignment with struts 114a, 114b, 114c, 114d, 114e, and 114f. Struts 114a, 114b, and 114c may be connected to one another in substantially end-to-end fashion diagonally along three cells 112, beginning with an end of the strut 114a connected to a commissure point 116 and ending with an end of strut 114c connected to an end of strut 114d. Struts 114c and 114d are part of the same cell 112 and may collectively define a substantially right angle between them. Struts 114d, 114e, and 114f may be connected to one another in substantially end-to-end fashion diagonally along three cells 112, beginning with an end of the strut 114f connected to a commissure point 116 and ending with the connection between an end of strut 114c and an end of strut 114d.

As discussed above, the leaflets 108 may be attached directly to and supported by the struts 114a, 114b, 114c, 114d, 114e, and 114f, such as by suturing. In such event, the cuff 106 may perform little or no supportive function for the leaflets 108. Hence, the cuff 106 is not subjected to high stresses and is therefore less likely to fail during use. In light of this, the thickness of the cuff may be reduced. Reducing the thickness of the cuff 106 results in a decrease in the volume of the valve assembly 104 in the collapsed condition. This decreased volume is desirable as it enables the prosthetic heart valve 100 to be implanted in a patient using a delivery device that is smaller than conventional delivery devices. In addition, since the material forming the stent struts 114 is stronger than the material forming the cuff 106, the stent struts 114 may perform the supportive function for the leaflets 108 better than the cuff 106.

The volume of the valve assembly 104 may be further reduced by having the cuff 106 cover only a portion of the surface of annulus section 110. With continued reference to FIG. 1, the first or proximal end 118 of the cuff 106 may substantially follow the contour of the first or proximal end 119 of the stent 102. As such, the proximal end of the cuff 106 may have a generally sinusoidal or zigzag shape. This eliminates any free edge of the cuff 106, which otherwise might extend directly between the cusps of the cells 112 at the proximal end 119 of the stent 102, and enables the entire length of the proximal end 118 of the cuff 106 to be secured to the stent 102. The second or distal end 120 of the cuff 106, on the other hand, may be disposed substantially along at least some struts 114, but not necessarily the struts in a single annular row of cells 112. More particularly, the distal end 120 of the cuff 106 may follow the stent struts 114 up to the commissure points 116, such that the cuff covers all of the cells 112 in the bottom annular row 113 of cells and in a second annular row 115 of cells located between the commissure points and the proximal end 119 of the stent 102, but covers a lesser area of cells in the annular regions between the commissure points. In other words, the distal end 120 of the cuff 106 may be disposed substantially along struts 114a, 114b, 114e, 114f, 114g and 114h, as shown in FIG. 1. Strut 114g may be connected at one end to strut 114h, and at the other end to the intersection of struts 114b and 114c. Strut 114h may be connected at one end to strut 114g, and at the other end to the intersection of struts 114d and 114e. Struts 114c, 114d, 114g, and 114h collectively form a single cell 112.

As a result of the foregoing configuration, all of the cells 112 in the bottom annular row 113 of cells may be entirely covered by the cuff 106. The cuff 106 may also entirely cover those cells 112 in the second annular row 115 that are located directly below the commissure points 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure points 116, there is little to no likelihood of leakage in the area of the cells between the commissure points in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

In operation, the embodiments of the prosthetic heart valve described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach. Once the delivery device has reached the target site, the user may deploy any of the prosthetic heart valves described above. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In a prosthetic heart valve, the valve assembly may be spaced from the distal or aortic end of the stent by a distance that enables deployment of the heart valve by an amount sufficient for the valve leaflets of the prosthetic valve to operate as intended, while the distal end of the stent remains captured by the delivery device. More particularly, as will be explained further below, the annulus end of the prosthetic heart valve may be deployed first, while the aortic end of the prosthetic heart valve remains at least partially covered by the distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus.

Figure 2:
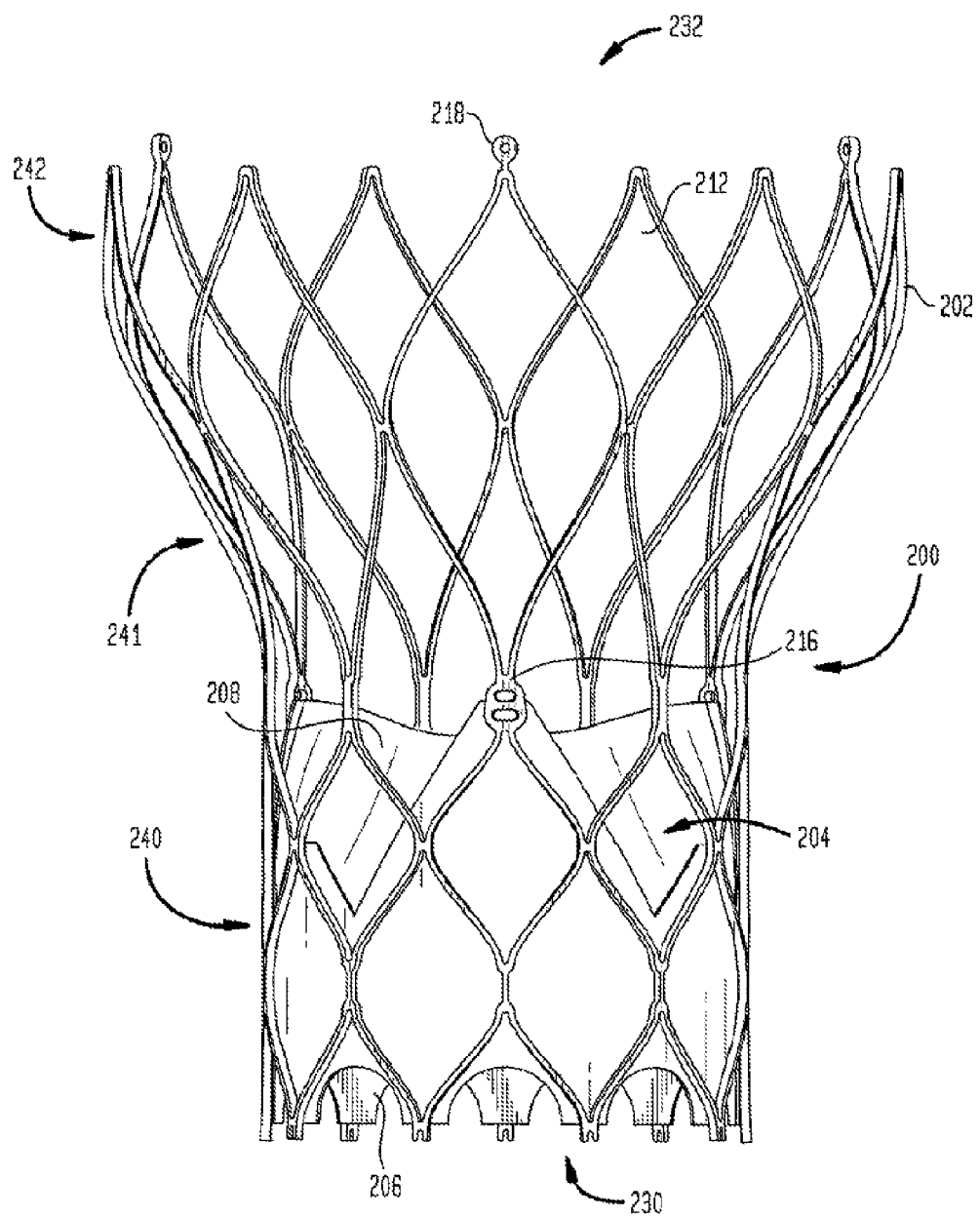
FIG. 2 is a partial side elevational view of a collapsible prosthetic heart valve according to an embodiment of the present invention, showing the valve assembly attached to the stent.

The features of this aspect of the present invention will be described in connection with the prosthetic heart valve 200 shown in FIG. 2. It will also be noted that while the inventions herein described are predominately discussed in terms of a tricuspid valve and a stent having a shape as illustrated in FIG. 2, the valve could be a bicuspid valve, such as the mitral valve, and the stent could have different shapes, such as a flared or conical annulus section, a less-bulbous aortic section, and the like, and a differently shaped transition section.

Prosthetic heart valve 200 includes an expandable stent 202 which may be formed from the same materials as each of the stents described above, and in particular, from those of the described materials that are capable of self-expansion. Stent 202 extends from a proximal or annulus end 230 to a distal or aortic end 232, and includes an annulus section 240 adjacent the proximal end, and an aortic section 242 adjacent the distal end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 may taper outwardly from the annulus section 240 to the aortic section 242. Each of the sections of the stent 202 includes a plurality of cells 212 connected to one another in one or more annular rows around the stent. For example, as shown in FIG. 2, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the distal end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The stent 202 may also include a plurality of commissure points 216 for attaching the commissure between two adjacent leaflets to the stent. As can be seen in FIG. 2, the commissure points 216 may lie at the intersection of four cells 212, two of the cells being adjacent one another in the same annular row, and the other two cells being in different annular rows and lying in end-to-end relationship. Preferably, commissure points 216 are positioned entirely within annulus section 240 or at the juncture of annulus section 240 and transition section 241. Commissure points 216 may include one or more eyelets which facilitate the suturing of the leaflet commissure to the stent.

The prosthetic heart valve 200 includes a valve assembly 204 positioned in the annulus section 240. Valve assembly 204 may be secured to stent 202 in the various manners described above. Valve assembly 204 includes a cuff 206 and a plurality of leaflets 208 which collectively function as a one-way valve. FIG. 2 illustrates a prosthetic heart valve for replacing a native tricuspid valve, such as the aortic valve. Accordingly, prosthetic heart valve 200 is shown in FIG. 2 with three leaflets 208, as well as three commissure points 216. However, it will be appreciated that the prosthetic heart valves according to this aspect of the invention may have a greater or lesser number of leaflets and commissure points.

Although cuff 206 is shown in FIG. 2 as being disposed on the lumenal surface of annulus section 240, it is contemplated that the cuff may be disposed on the ablumenal surface of annulus section 240, or may cover all or part of either or both of the lumenal and ablumenal surfaces of annulus section 240. Both the cuff 206 and the leaflets 208 may be wholly or partly formed of any suitable biological material or polymer, including those, such as PTFE, described above in connection with prosthetic heart valve 100.

As is shown in FIG. 2, in one embodiment the entirety of valve assembly 204, including the leaflet commissures, is positioned in the annulus section 240 of stent 202. When opened, the leaflets may extend further into the transition region or may be designed such that they remain substantially completely within the annulus region. That is, substantially the entirety of valve assembly 204 is positioned between the proximal end 230 of stent 202 and the commissure points 216, and none of the valve assembly 204 is positioned between commissure points 216 and the distal end 232 of the stent.

Indeed, in some embodiments, the valve can be designed such that, upon partial deployment, the commissure points are fully exposed, oriented generally parallel to the direction of blood flow, and at or near their actual radially expanded position (but not necessarily their eventual position relative to the annulus), such that the leaflets can operate substantially as they would when the valve is fully deployed, even though enough of the stent is still retained within the delivery device or sheath to permit resheathing.

In a preferred arrangement, the distance between commissure points 216 and the distal end 232 of stent 202 will be about two-thirds of the length of the stent from the proximal end 230 to the distal end. This structural arrangement provides advantages in the deployment of prosthetic valve 200 as will be discussed in more detail with reference to FIGS. 3A and 3B. By having the entirety of valve assembly 204 positioned within annulus section 240, and by having a sufficient distance between commissure points 216 and the distal end 232 of stent 202, the valve assembly and commissures will not impede blood flow into the coronary arteries and will not interfere with access thereto during cardiac intervention, such as angiography, annuloplasty or stent placement.

Further, it is possible to partially deploy prosthetic valve 200 so that the valve assembly 204 thereof is able to fully function in its intended position in the native valve annulus, while a sufficient amount of the aortic section 242 is retained within the delivery device should resheathing become necessary. In other words, as will be explained in more detail below, the user may withdraw the distal sheath of the delivery device to gradually expose prosthetic valve 200, beginning at the proximal end 230. Continued withdrawal of the distal sheath will expose a greater extent of the prosthetic valve until the entire annulus section 240 and valve assembly 204 have been exposed. Upon exposure, these portions of the prosthetic valve will expand into engagement with the native valve annulus, entrapping the native valves, except for a small portion immediately adjacent the free end of the distal sheath which will be constrained by the distal sheath from fully expanding.

However, once the distal sheath has been withdrawn to expose a sufficient portion of the aortic section 242, the annulus section 240 will be able to fully expand and valve assembly 204 will be able to function in the same manner as if the entirety of prosthetic valve 200 had been deployed. At this juncture, it will be possible for the user to ascertain whether annulus section 240 and valve assembly 204 have been properly positioned relative to the native valve annulus, and whether the valve assembly is functioning properly.

If the position and operation of valve assembly 204 are acceptable, the distal sheath may be withdrawn further to deploy the remainder of prosthetic valve 200. On the other hand, if the positioning or operation of valve assembly 204 is unacceptable, the user may advance the distal sheath to resheath the prosthetic valve, reposition same and initiate the deployment procedure anew. And if it is determined that the valve is not functioning properly, it can be withdrawn from the patient and a new valve introduced.

Figure 3A:
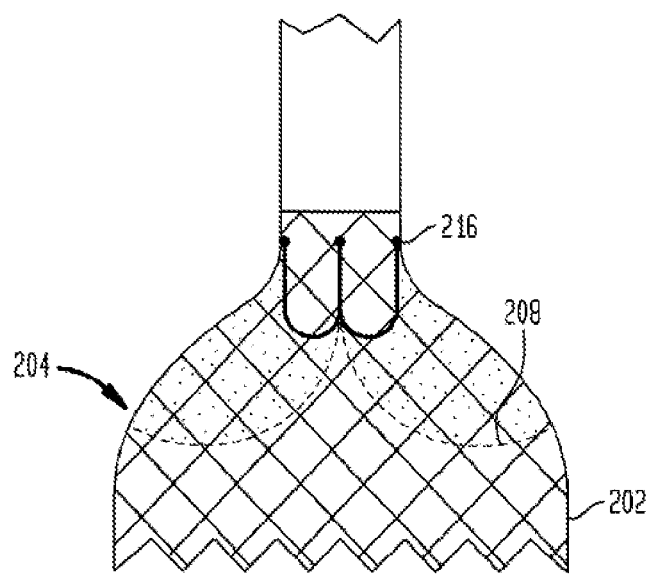
FIG. 3A is a side elevational view showing partial deployment of a collapsible prosthetic heart valve with high placement.
Figure 3B:
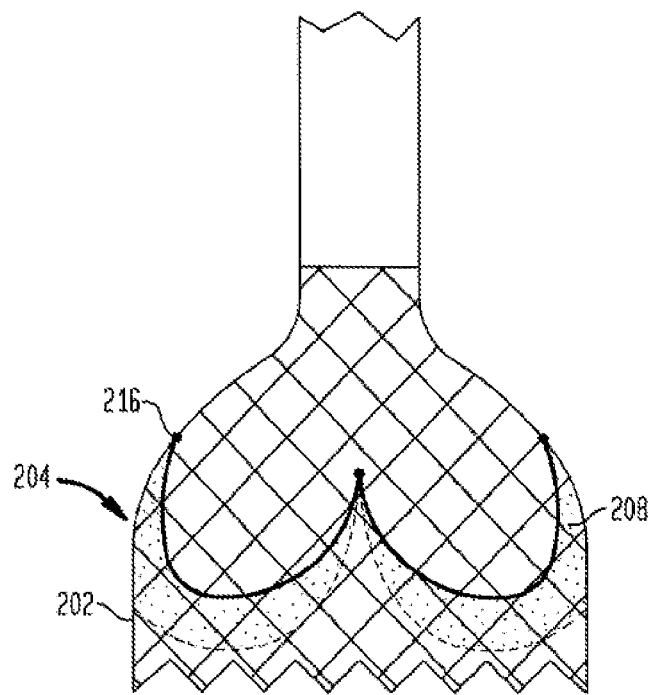
FIG. 3B is a side elevational view showing partial deployment of a collapsible prosthetic heart valve with low placement.

Stated another way, as shown in FIGS. 3A and 3B, the placement of the leaflets 208 within the stent 202 can affect the valve functioning during partial deployment. FIG. 3A illustrates a valve assembly 204 with high placement, while FIG. 3B illustrates a valve assembly with low placement according to one embodiment of the present invention. As used herein the phrase "high placement" of a valve assembly refers to locating the valve assembly within the transition section 241 of the stent 202, or the portion of the annulus section 240 closest to the transition section. The phrase "low placement" of a valve assembly refers to locating the valve assembly closer to the proximal end 230 of the stent 202 and entirely within the annulus section 240 thereof, such that the leaflets 208 are substantially disposed within the annulus section 208.

As seen in FIG. 3A, during partial deployment the annulus end of the heart valve 200 is unsheathed and allowed to expand. The distal end 232, including the aortic section 242, remains partially sheathed and coupled to the delivery device. Operation of the delivery device is described below in more detail with reference to FIGS. 11-22. Turning back to FIG. 3A, it will be appreciated that high placement of valve assembly 204 will cause the valve assembly to not be fully deployed when heart valve 200 is only partially deployed, thereby affecting leaflet function. Specifically, since the commissure points 216 are located closer to or within the transition section 241, they do not reach their fully expanded positions. As such, the leaflets 208 that are attached to commissure points 216 remain partially closed. Because of the location of the commissure points 216 and the leaflets 208, the valve assembly 204 cannot be tested during partial deployment. Instead, the user must unsheath a portion of the aortic section 242 as well, which may pose problems if the valve assembly 204 is to be resheathed and redeployed.

In contrast to the prosthetic heart valve of FIG. 3A, the heart valve 200 of FIG. 3B exhibits low placement of the valve assembly 204 within the annulus section 240. Low placement of the valve assembly 204 enables the valve assembly to fully deploy when heart valve 200 is only partially deployed. As such, commissure points 216 and the leaflets 208 attached to same reach their fully expanded and open positions and are able to function near normally, enabling a better assessment of the valve's functioning and final placement within the actual anatomy. Thus, if it appears that the valve needs to be moved, the heart valve 200 may be easily resheathed and repositioned. This concept is beneficial when dealing with less than ideal anatomical configurations as will be discussed below with reference to FIGS. 5-9.

The shape of the stent 202 during partial deployment will also affect the valve 204. If the stent shape is such that, while still partially retained by the sheath, it cannot open sufficiently to allow operation of the valve, it may not be possible to fully assess the operation of the valve in its intended placement position. Moreover, the height of the valve commissures 216 relative to the proximal end 230 of the valve will affect the valve function. The lower the commissures 216, meaning the closer to the proximal end 230, the more they will expand outwardly and the valve leaflets will be able to open during partial deployment, creating a flow passageway through the leaflets which approaches that of a fully deployed valve. The relationship of stent shape, commissure height and valve location to flow passageway will be more fully discussed below with reference to FIGS. 4A and 4B.

Figure 4B:
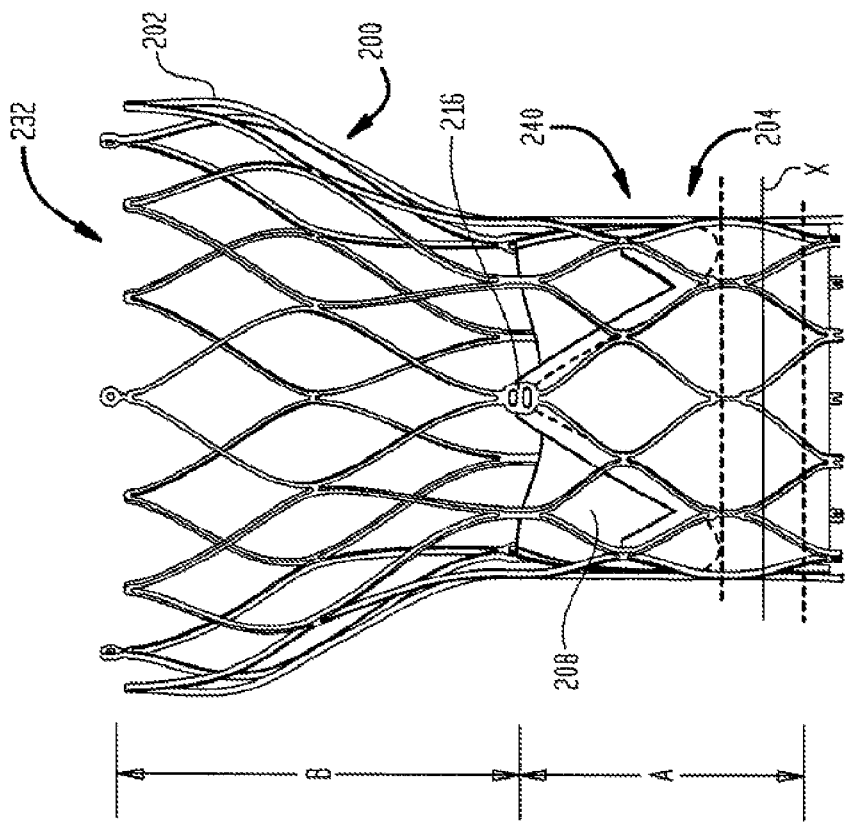
FIG. 4B is a side elevational view of a collapsible prosthetic heart valve according to the present invention.
Figure 4A:
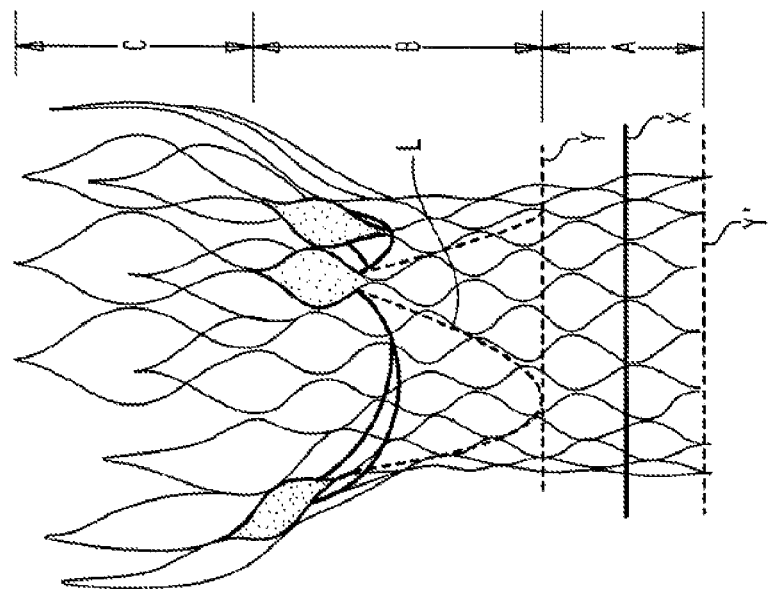
FIG. 4A is a side elevational view of a conventional collapsible prosthetic heart valve.

FIGS. 4A and 4B illustrate a publicly known prosthetic heart valve available from Medtronic/CoreValve and a prosthetic heart valve 200 in accordance with one embodiment of the present invention, respectively. Prosthetic heart valve 200 shown in FIG. 4B is substantially the same as the prosthetic heart valve 200 shown in FIG. 2 and described above, but is repeated here to show a side-by-side comparison with the prosthetic heart valve of FIG. 4A. See also United States Patent Application Publication No. 2006/0259136 to Nguyen et al. and, in particular, FIG. 6 thereof. The greater the distance between the valve assembly and the distal end of the stent (the end of the stent to be disposed in the aorta or aortic sinus, furthest from the heart), the greater the chance the valve will open and operate in a substantially normal fashion during partial deployment. The greater the distance the free end of the sheath is from the valve assembly during partial deployment, the more the stent 202 can expand to a size and shape conducive for valve operation. Thus, the further the valve assembly 204 can be positioned from the free end of the delivery sheath during partial deployment, the better the flow through the valve.

Figure 6:
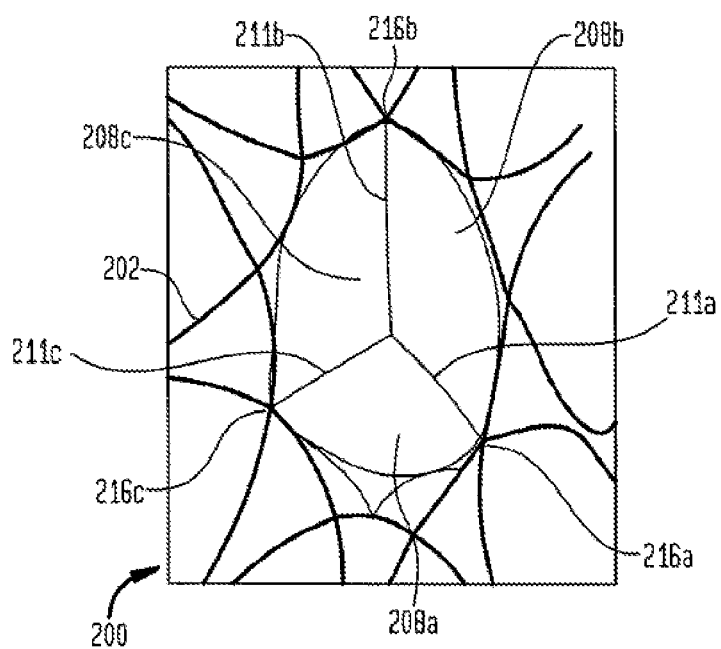
FIG. 6 is an end view of the prosthetic heart valve of FIG. 2 as seen from the aortic sinus toward the heart and the native valve annulus, the valve being disposed in an elliptical configuration.

The CoreValve device, as shown in FIG. 4A hereof and FIG. 6 of the aforementioned patent publication, has commissure supports that extend up into the transition or sinus region of the device. Therefore, it is possible that part of the valve assembly itself will still be contained within the delivery sheath during partial deployment of approximately two-thirds of the overall length of the valve. Even if that is not the case, it is believed that the sheath will exert sufficient influence on the stent and, with it, the valve assembly, to prevent the valve from functioning properly unless more fully deployed.

As shown in FIG. 4B, the prosthetic valve 200 in accordance with the present invention contains a valve assembly 204 disposed more completely within the annulus section 240. Thus, if the same approximately two-thirds of the length of the valve is exposed for partial deployment, the distance of the valve assembly 204 from the free end of the delivery sheath, coupled with the positioning of the valve assembly and the commissure points 216 in the annulus section 240, allows for functional operation of the valve to be observed even during partial deployment.

Specifically, as illustrated in FIG. 4B, the placement of the valve assembly 204 in the annulus section of prosthetic valve devices in accordance with the invention may provide additional benefits. In FIGS. 4A and 4B, the annulus between the left ventricle and the aortic sinus of the native valve is represented by the line labeled "X". The valve in FIG. 4A includes leaflets, represented by the dashed line labeled "L", disposed a significant distance from the proximal or inlet end of the valve. The leaflets L are attached near the upper edge Y of a cuff positioned on the lumenal surface of the valve stent. The commissure supports for the valve leaflets are attached relatively higher in the transition region of the stent. The portion of the valve to be implanted in the native valve annulus, shown between dashed lines Y and Y', is wide. But, if seated high (i.e., with dashed line Y' relatively close to native valve annulus X), the commissure supports could interfere with access to the coronary arteries. See FIG. 6 of United States Patent Publication No. 2006/0259136. If seated lower such that the valve leaflets are closer to the location of the native leaflets (i.e., with dashed line Y relatively close to native valve annulus X), the valve will protrude into the left ventricle and could interfere with the operation of the mitral valve or otherwise interfere with proper cardiac functioning. By comparison, in the embodiment of the invention illustrated in FIG. 4B, the leaflets 208 are attached within the valve assembly 204 and the commissure points 216 are located in the annulus section 240 such that, when implanted, the prosthetic valve will neither block the coronary arteries nor protrude into the left ventricle in a way that will cause an impediment.

Stated differently, the prosthetic valve in FIG. 4A may be described as having three portions between the proximal and distal ends: an annulus portion A, an intermediate portion B and an aortic portion C. The annulus portion A extends from the proximal end of the valve to the point of attachment between the stent and the leaflets L. The second portion B extends from the point of attachment between the stent and the leaflets L to the distalmost end of the commissure points. The aortic portion C extends from the distalmost end of the commissure points to the distal end of the valve. As seen in FIG. 4A, the commissure points are located about one-third of the overall length of the valve from the distal end, and the intermediate portion B containing the valve leaflets L is disposed about halfway between the valve's proximal and distal ends. In contrast, the valve 200 of FIG. 4B includes a portion B that extends from the commissure points 216 to the distal end 232 of the valve with the commissure points being positioned about two-thirds of the overall length of the valve from the distal end. Moreover, as seen in FIG. 4B, the valve leaflets 208 are disposed substantially in the annulus section 240, which occupies about one-third of the overall length of the valve farthest from the distal end 232.

As discussed above, the positioning of the valve assembly 204, commissure points 216 and leaflets 208 within the stent 202 affects the effectiveness of the valve during partial deployment. The preceding embodiments allow for better assessment of the functioning of the valve before full deployment. The concepts discussed above with regard to the positioning of the valve assembly 204, the commissure points 216 and the leaflets 208 within stent 202 provide additional improvements in coaptation of the leaflets 208.

In certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid disease, and/or valve insufficiency could not be treated well, if at all, with the current collapsible designs.

The reliance on evenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology.

Figure 5:
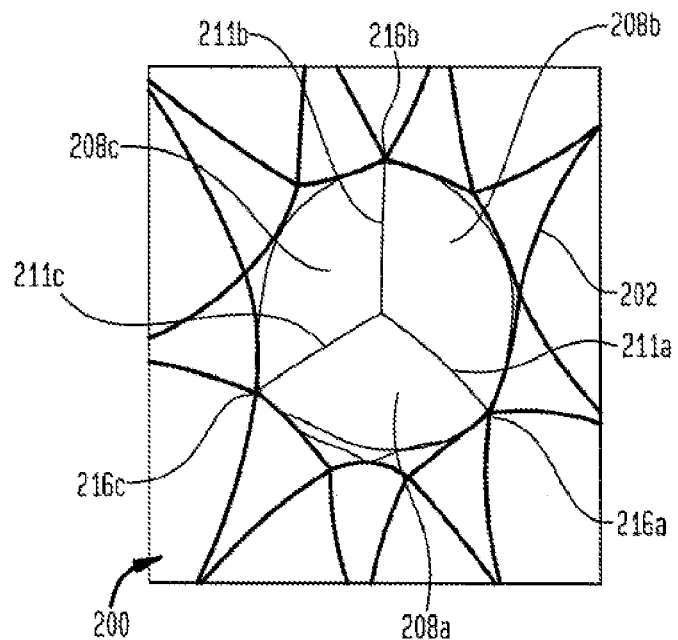
FIG. 5 is an end view of the prosthetic heart valve of FIG. 2 as seen from the aortic sinus toward the heart and the native valve annulus, the valve being disposed in a circular configuration.
Figure 7B:
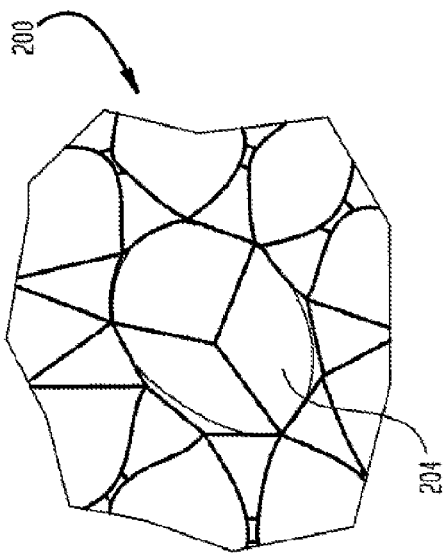
FIG. 7B is an end view of the prosthetic heart valve of FIG. 2 in a second configuration as seen from the aorta or aortic sinus toward the heart and the native valve annulus.
Figure 7D:
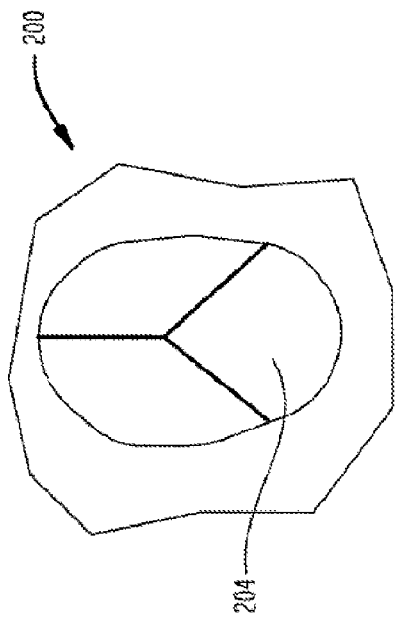
FIG. 7D is an end view of the prosthetic heart valve disposed in the configuration of FIG. 7B as seen from the left ventrical, looking up toward the aortic sinus.
Figure 7A:
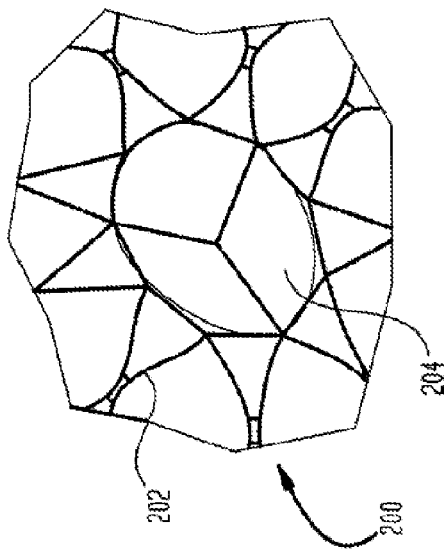
FIG. 7A is an end view of the prosthetic heart valve of FIG. 2 in a first configuration as seen from the aorta or aortic sinus toward the heart and the native valve annulus.
Figure 7C:
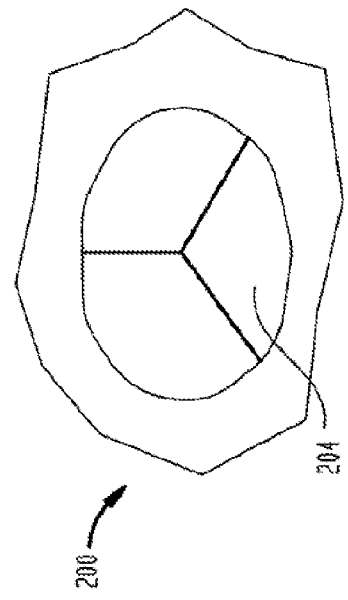
FIG. 7C is an end view of the prosthetic heart valve disposed in the configuration of FIG. 7A as seen from the left ventrical, looking up toward the aortic sinus.

One potential solution is a valve that could be partially deployed to assess the above-mentioned issues before full deployment. This has already been discussed. Another potential solution, which can be employed alone or with the ability to partially deploy, is the use of a design which provides for suitable coaptation even in less than ideal settings. FIGS. 5 and 6 illustrate such a valve. The figures show an end view of the prosthetic valve 200 of FIG. 2 as seen from the downstream side of the valve assembly 204, e.g., looking from the aorta or aortic sinus toward the heart and the native valve annulus. See also FIGS. 7A and 7B, which provide a similar view of an embodiment of a valve 200. FIGS. 7C and 7D provide an end view of the valve 200 of FIGS. 7A and 7B as seen from the upstream direction, e.g., looking from the left ventrical toward the aorta. FIGS. 7C and 7D illustrate, in particular, the annulus section of stent 202 and the valve assembly 204, including the cuff 206, from that perspective.

The valve assembly 204 includes valve leaflets 208a, 208b, and 208c attached to commissure points 216a, 216b, and 216c. The valve leaflets 208a-c are attached to the stent 202 in any of the configurations previously described. At least one edge of each leaflet 208 is sutured to the stent 202 and to two of the three commissure points 216, leaving at least one edge free to move in response to the pumping of blood. As the blood pressure in the left ventricle increases, the free edges of the leaflets move away from one another to allow blood to flow from the left ventricle to the aorta, following which the free edges move toward one another and coapt to prevent blood from flowing back from the aorta into the left ventricle.

It will be understood that the coaptation of "the free edges" of the valve leaflets does not necessarily mean that the actual edges meet per se. Indeed, the leaflets are preferably sized, shaped, and attached such that a suitable "belly" contour is formed. And the leaflets should each include a portion extending from the free edge toward the annulus (referred to herein as a "coaptation section") that may engage the coaptation sections of the other leaflets such that there will be a surface area of contact between the leaflets rather than edge-to-edge contact. This surface area of contact is important so that, when in a closed or "coapted" condition, the leaflets cooperate to substantially prevent backflow or regurgitation of blood through the valve. These areas of actual contact between the coaptation sections of adjacent leaflets are referred to herein as the coaptation junctions of the leaflets and are illustrated in FIG. 5 at 211a, 211b, and 211c. The coaptation section of each leaflet may range in size as a particular valve design demands, but generally will be sufficient to provide some tolerance or ability to form a coaptation junction even if the shape of the valve is distorted during placement, as illustrated in FIG. 6.

As shown previously in FIG. 2, the annulus section 240 of prosthetic valve 200 has a generally regular cylindrical shape by which is meant that the structure has a generally circular cross-section with a substantially constant diameter along its length. When placed in the annulus of a native heart valve, such as, for example, the tricuspid aortic valve, and expanded, a substantially fluid-tight fit should result. However, the native valve annulus may not be circular, and, in fact, may vary from patient to patient, as may the shape of the aortic sinus or aorta, the angle of the junction between the valve annulus and the aortic sinus, and other local anatomical features. When prosthetic valve 200 is deployed and expanded, it must accommodate these anatomical variations in order to function properly. This may result in a distortion in the shape of stent 202 and/or valve assembly 204, and the repositioning of leaflets 208a, 208b, and 208c relative to one another, which can affect the coaptation junctions 211a, 211b, and 211c.

As the stent of a collapsible prosthetic heart valve distorts during implantation, during beating of the heart, or because of irregularities in the patient's anatomy or the condition of the native valve, such distortion may be translated to the valve assembly, such that not all of the valve leaflets meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets, can be postulated.

Prosthetic valves in accordance with certain aspects of the present invention, however, can function properly notwithstanding the distortion of the stent 202 and/or valve assembly 204. For example, as shown in FIG. 6, valve leaflets 208a, 208b, and 208c fully coapt despite the distortion of the annulus section 240 (hidden behind the valve leaflets in this figure) into a more elliptical configuration. As will be appreciated, the distortion of the annulus section 240 affects the relative positions of commissure points 216a-c, as well as the positions of leaflets 208a-c relative to one another. The ability of the valve leaflets 208a-c to fully coapt despite this distortion enables prosthetic valve 200 to function in the manner intended.

Although FIG. 6 illustrates a situation in which annulus section 240 has been distorted such that the major axis of the resulting ellipse or irregular shape is substantially parallel to coaptation junction 211b, that need not be the case. Depending on the shape of the native valve annulus and the orientation in which the prosthetic valve is deployed, the annulus section 240 and/or the valve assembly 204 may be distorted such that the major axis of the resulting shape is oriented in any radial direction relative to the longitudinal axis of the prosthetic valve. As can be appreciated from FIGS. 7A-D, regardless of the direction of distortion, valve leaflets 208a-c are able to fully coapt and prosthetic valve 200 is able to function properly. The valve leaflets 208a-c are capable of effective engagement along coaptation junctions 211a-c in any anatomical configuration of the native valve annulus, such as circular, elliptical, ovoid or any other curved configurations.

Figure 8A:
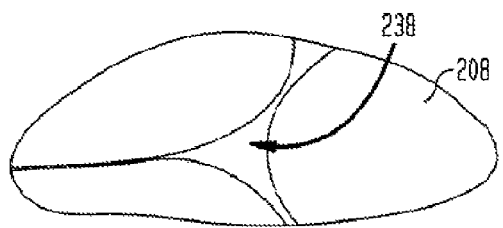
FIG. 8A is an end view of a conventional prosthetic heart valve having a shallow belly contour illustrating inadequate coaptation.
Figure 8B:
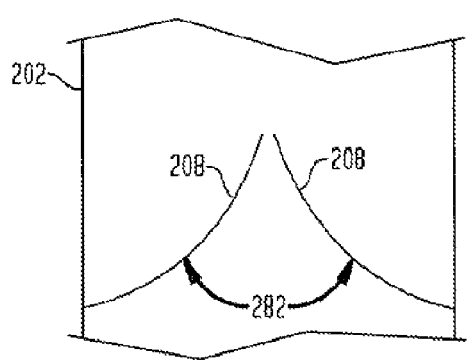
FIG. 8B is a side elevational view of the conventional prosthetic heart valve of FIG. 8A showing inadequate coaptation.

A comparison between FIGS. 8A-B and FIGS. 8C-D illustrates the difference between inadequate coaptation of a conventional prosthetic valve and superior coaptation of a prosthetic valve according to one embodiment of the present invention. As will be appreciated from FIGS. 8A and 8B, the leaflets 208 of a conventional device are incapable of complete coaptation when disposed in a native valve annulus with an elliptical, ovoid or otherwise non-circular configuration. Specifically, a shallow belly contour 282 as seen in FIG. 8B creates a gap 238 between the leaflets 208. The end view seen in FIG. 8A illustrates inadequate coaptation which may lead to leakage and regurgitation as discussed above.

Figure 8C:
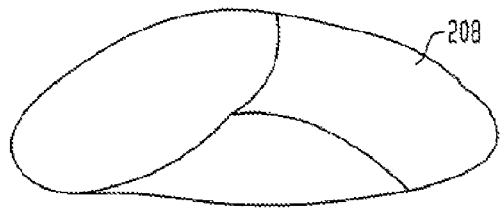
FIG. 8C is an end view of one embodiment of a prosthetic heart valve having a belly contour according to the present invention showing superior coaptation.
Figure 8D:
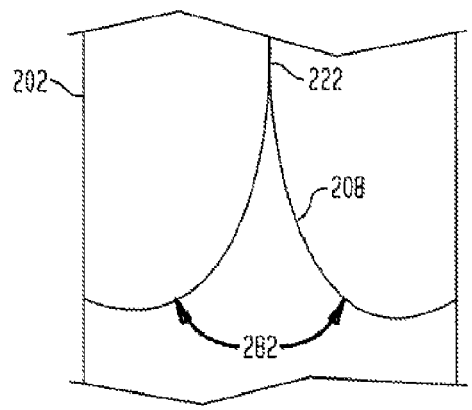
FIG. 8D is a side elevational view of the prosthetic heart valve of FIG. 8C showing superior coaptation.

By way of comparison, the leaflets 208 seen in FIGS. 8C and 8D provide superior coaptation. Specifically, the leaflets 208 of FIGS. 8C and 8D are slightly elongated and include a deeper belly contour 282, forming a coaptation section 222. As used herein the term "belly contour" refers to the curvature of the leaflets 208. The leaflets 208 according to one embodiment of the present invention include a belly contour that is curved concavely toward the distal end of the stent. The curvature of the leaflets 208 may affect the coaptation of the leaflets. In some embodiments, a smaller radius of curvature is preferred. As seen in the end view of FIG. 8C, the leaflets 208 merge smoothly and no gap is formed between the leaflets in the closed position. The deeper belly contour 282 and the leaflets 208 having coaptation sections 222 allow the leaflets to adequately coapt regardless of the shape or configuration of the native valve annulus. In at least some embodiments, the leaflets form a coaptation section 222 that is substantially parallel to the longitudinal axis of the valve. The leaflets 208 may be configured such that a steep belly contour 282 is formed. Though the curvature of the leaflets 208 may vary, a steeper belly contour 282 may be preferable to a shallow belly contour. The curvature of the leaflets 208 in the closed position may be modeled by a mathematical function (e.g., exponential or polynomial functions).

Figure 9A:
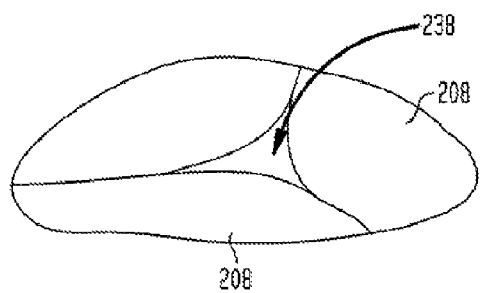
FIG. 9A is an end view of a conventional prosthetic heart valve having a flat belly illustrating inadequate coaptation.
Figure 9B:
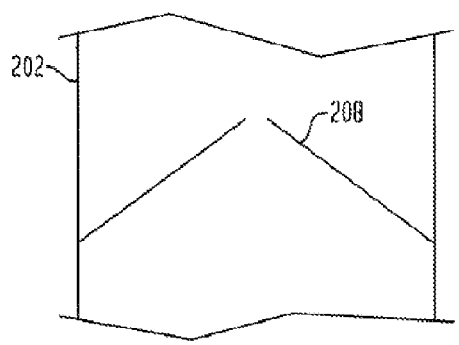
FIG. 9B is a side elevational view of the conventional prosthetic heart valve of FIG. 9A showing inadequate coaptation.
Figure 9C:
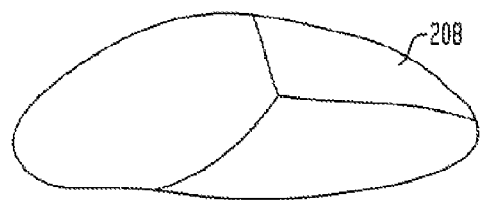
FIG. 9C is an end view of one embodiment of a prosthetic heart valve having a flat belly according to the present invention showing superior coaptation.

FIGS. 9A-9D illustrate the difference between inadequate coaptation of a conventional prosthetic valve and superior coaptation of a prosthetic valve according to a second embodiment of the present invention. As seen in FIGS. 9A and 9B, the leaflets 208 of the valve do not include a shallow belly contour as seen in FIG. 8B. Instead, the leaflets of FIGS. 9A and 9B are flat. Due to an elongated axis or irregular shape (e.g., the native valve annulus being elliptical), the leaflets 208 in FIG. 9B do not fully contact or merge. The result, as seen in FIG. 9A, is a gap 238 between the leaflets 208 similar to that formed in the valve of FIG. 8A. In contrast, the embodiment shown in FIGS. 9C and 9D includes a flat belly (e.g., none of the belly contour seen in FIGS. 8C-D), and a coaptation section 222 that provides a level of tolerance in case of an elongated axis or irregular shape. The leaflets 208 form a first flat belly section 292 angled toward the center of the valve and a second coaptation section 222 that is substantially parallel to the longitudinal axis of the valve. The leaflet coaptation section 222 compensates for an elongated axis and provides adequate coaptation between the leaflets 208.

Figure 9D:
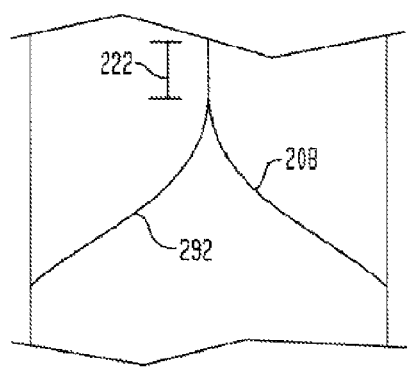
FIG. 9D is a side elevational view of the prosthetic heart valve of FIG. 9C showing superior coaptation.

The coaptation section 222 as shown in FIG. 9D may range from about 1 mm to about 5 mm in length in a direction from the free edge of the leaflet 208 toward the stent 202. Preferably, the coaptation section will be about 1.5 mm to about 4 mm in length, and more specifically about 2 mm to about 3.5 mm in length. As discussed above, the coaptation section 222 may be configured such that when the leaflets 208 are brought together in a closed state of the valve, the coaptation section 222 forms a segment that is substantially parallel to the longitudinal axis of the valve. In at least some embodiments, the coaptation section 222 occupies about 10% to about 30% of the total length of each leaflet 208.

Without being bound by any particular theory, it is believed that several factors and unique design attributes of prosthetic valve 200 contribute to its adaptability to variations in the natural anatomy of the patient as exemplified in FIG. 6. The commissure points 216a, 216b, and 216c are not elongated posts or bars and are integrated into the superstructure of stent 202 such that they, individually and collectively, do not negatively impact the flexibility of the stent. Because the commissure points 216a-c and the valve leaflets 208a-c are both disposed within, or substantially within, the annulus section 240, anatomical irregularities in the aorta and/or the aortic sinus will have relatively less impact on the coaptation junctions 211a-c than if these valve components were positioned in or extended into the transition section 241 or the aortic section 242. Furthermore, because the cross-section of the native valve annulus is typically less than the cross-section of the aortic sinus, the range of variations in the native valve annulus to which the prosthetic valve must adapt will ordinarily be less than in the aortic sinus.

Moreover, as the commissure points 216a-c and valve leaflets 208a-c are disposed within or substantially within the annulus section 240, the coaptation junctions 211a-c will be influenced little, if at all, by any irregularities in the junction between the native valve annulus and the aortic sinus (such as where the aortic sinus is skewed at an angle to the native valve annulus).

In addition, the location of the commissure points 216a-c in the annulus section 240, or immediately adjacent thereto, and the attachment of the valve assembly 204 within that section, as illustrated in FIG. 2, helps restrict the degree of movement of one leaflet relative to another. If the commissure points 216a-c were disposed higher, such as in the transition section 241 or the aortic section 242 of the prosthetic valve, then any deformation of the annulus section 240, which would result in an overall deformation of the stent 202, could cause a larger relative movement of, for example, the commissures. This could overwhelm any reasonable overlap that may be present in the coaptation junctions 211a-c of the valve leaflets 208, reducing their likelihood of coaptation. Thus, the change in shape of the stent would be magnified and this would further magnify the effect on the relative positions of the valve leaflets 208a-c and their coaptation junctions 211a-c. By keeping the valve assembly substantially within the annulus section 240, these magnifying influences can be suppressed.

In addition to coaptation issues, anatomical and positional irregularities can create issues with respect to the proper functioning and wear of the prosthetic valve. Another aspect of the invention is achieving a better functioning valve in these various shapes, such as elliptical, round, ovoid, irregular, etc.

As illustrated in FIGS. 8A-D and 9A-D, the valve shape, size and configuration are also important in ensuring that the valve functions properly even when implanted in a less than ideal geometry. The amount of leaflet material provided should be sufficient to allow for the creation of a "leaflet belly" having a parabolic-like contour. Sufficient leaflet material must be used to ensure that there is a sufficient length of free edge between adjacent commissure points 216, and also to provide a sufficient belly contour 282 such that the coaptation junctions of the leaflet can properly form a coaptation section 222, even when the relative alignment of the leaflets is disturbed from an ideal alignment. Too shallow a belly contour 282 may lead to a central gap 238, a break in the coaptation junction between adjacent leaflets and/or put too much load or stress on the leaflet at the point of attachment to the commissure point.

Figure 10:
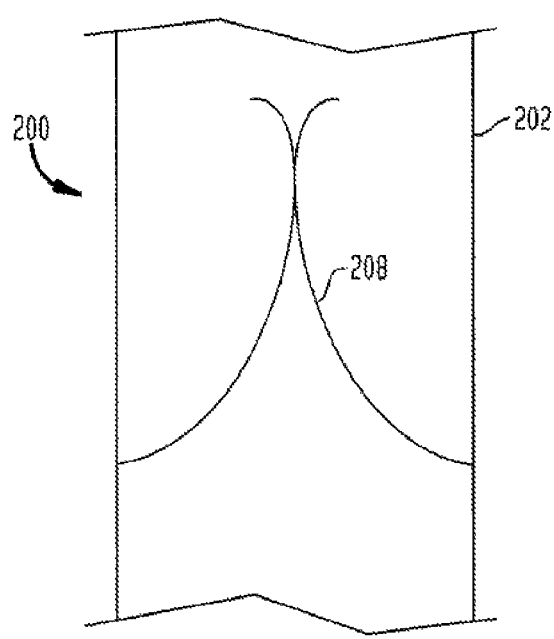
FIG. 10 is a side elevational view of a prosthetic heart valve having extended coaptation sections with free edges that interfere with coaptation.
Figure 11:
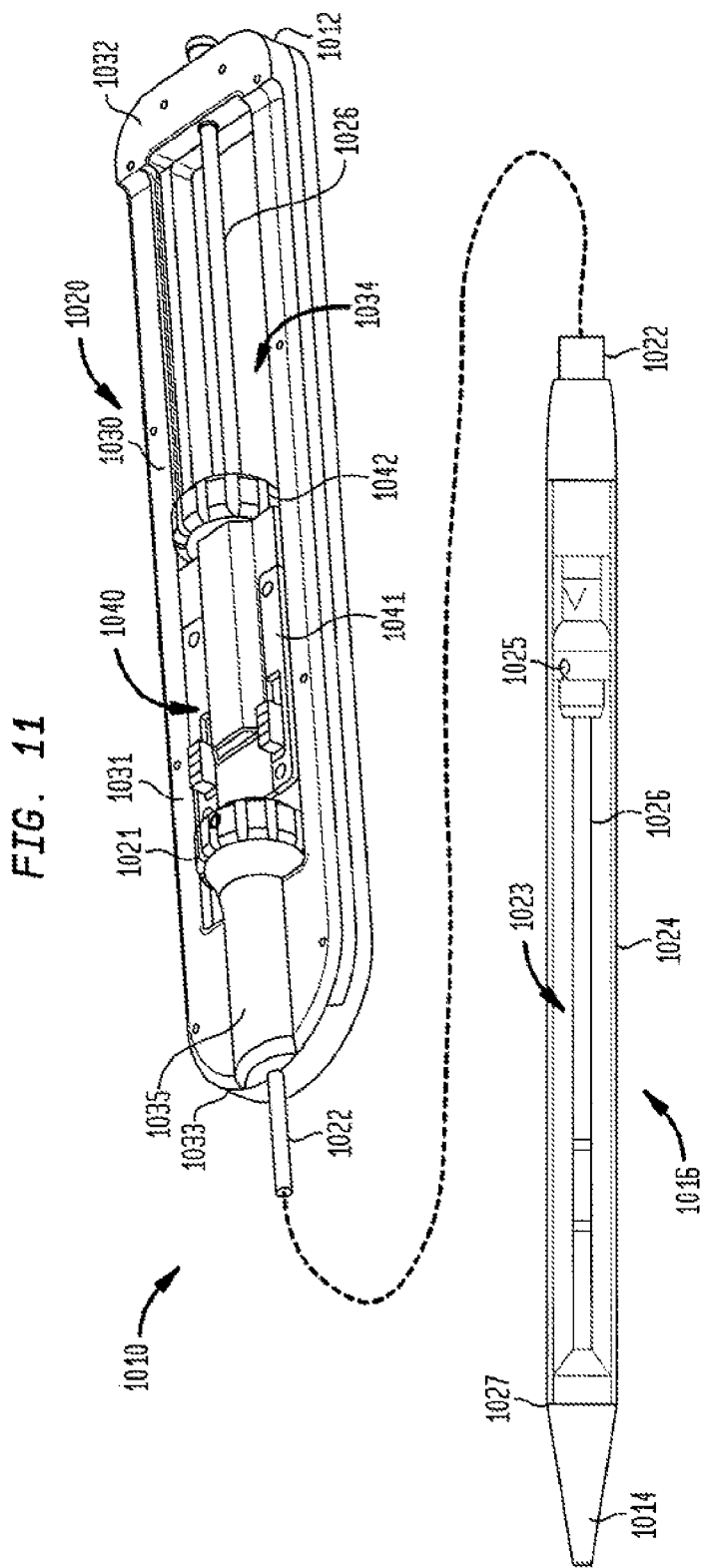
FIG. 11 is a perspective view of an operating handle for a transfemoral delivery device for a collapsible prosthetic heart valve, shown with a side elevational view of the distal portion of a transfemoral catheter assembly.
Figure 12:
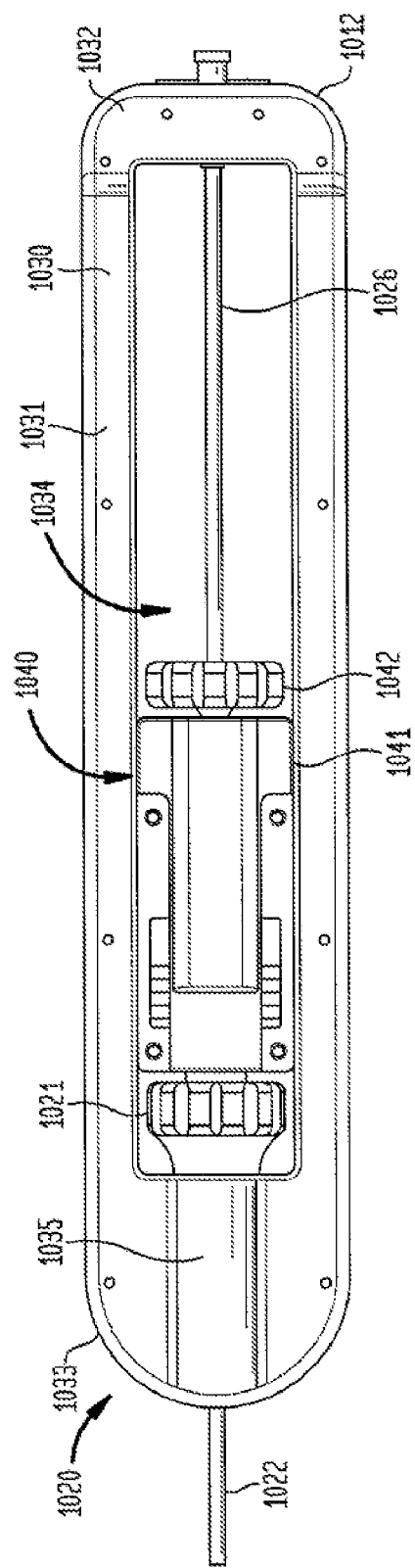
FIG. 12 is a top plan view of the handle of FIG. 11.
Figure 13:
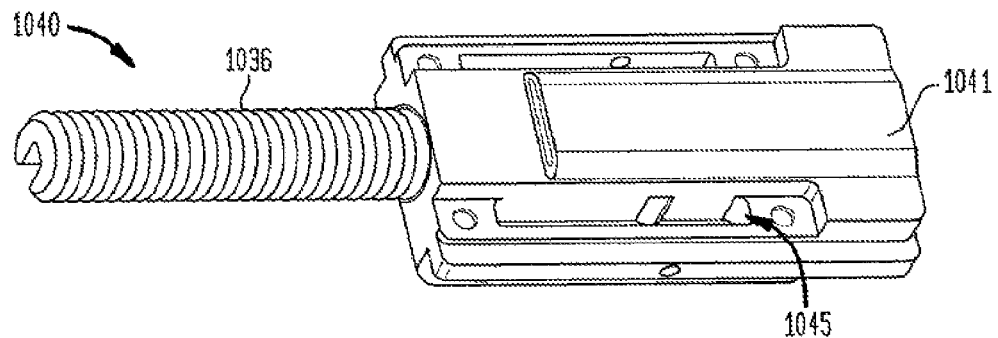
FIG. 13 is an enlarged perspective view of the carriage assembly of the handle of FIG. 11.
Figure 14:
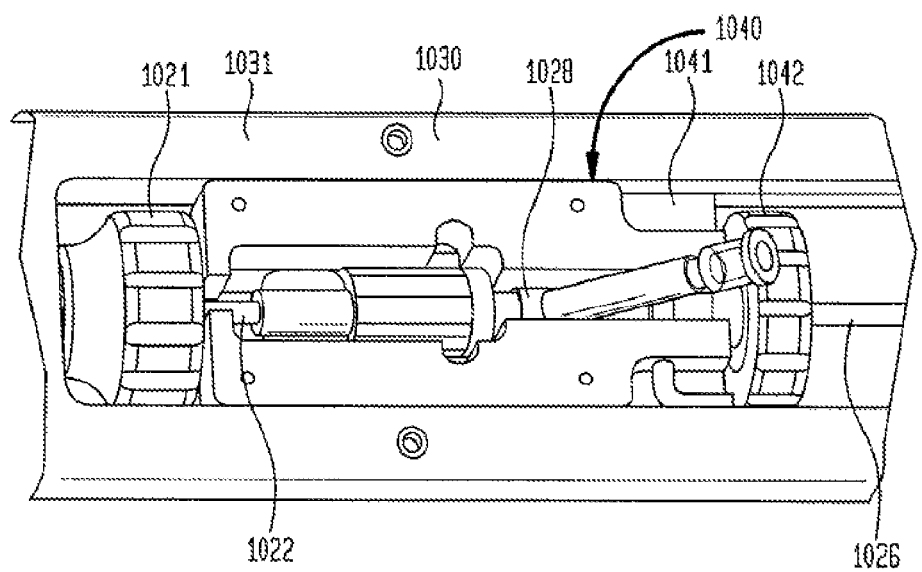
FIG. 14 is an enlarged bottom perspective view of a portion of the handle of FIG. 11.

Yet, the coaptation section 222 should not be so large so as to produce a free edge that curls over, interferes with coaptation, or extends too far into the transition section of the stent. For example, FIG. 10 illustrates a side elevational view of a prosthetic valve 200 having leaflets 208 with poor coaptation and excess slack. The leaflets of FIG. 10 angle toward the center of the valve and coapt, but come apart at their free ends, outwardly curling over the coaptation section 222. Such a configuration may interfere with coaptation or negatively affect flow through the valve. Thus, it will be understood that the shape and configuration of the leaflets 208 and the coaptation sections 222 ought to be within a favorable range as described above.

A transfemoral or transapical delivery device may be used to partially deploy the prosthetic heart valve such that an assessment may be made regarding flow through the valve and adequacy of coaptation. If, after the annulus section is unsheathed and the valve is tested, it is found that the valve needs to be repositioned, the annulus section may be resheathed and the valve redeployed as necessary.

Turning now to FIGS. 11-14, an exemplary transfemoral delivery device 1010 for a collapsible prosthetic heart valve (or other types of self-expanding collapsible stents) has a catheter assembly 1016 for delivering the heart valve to and deploying the heart valve at a target location, and an operating handle 1020 for controlling deployment of the valve from the catheter assembly. The delivery device 1010 extends from a proximal end 1012 to a distal tip 1014. The catheter assembly 1016 is adapted to receive a collapsible prosthetic heart valve (not shown) in a compartment 1023 defined around an inner shaft 1026 and covered by a distal sheath 1024.

The inner shaft 1026 extends through the operating handle 1020 to the distal tip 1014 of the delivery device, and includes a retainer 1025 affixed thereto at a spaced distance from distal tip 1014 and adapted to hold a collapsible prosthetic valve in the compartment 1023.

The distal sheath 1024 surrounds the inner shaft 1026 and is slidable relative to the inner shaft such that it can selectively cover or uncover the compartment 1023. The distal sheath 1024 is affixed at its proximal end to an outer shaft 1022, the proximal end of which is connected to the operating handle 1020 in a manner to be described. The distal end 1027 of the distal sheath 1024 abuts the distal tip 1014 when the distal sheath is fully covering the compartment 1023, and is spaced apart from the distal tip 1014 when the compartment 1023 is at least partially uncovered.

The operating handle 1020 is adapted to control deployment of a prosthetic valve located in the compartment 1023 by permitting a user to selectively slide the outer shaft 1022 proximally or distally relative to the inner shaft 1026, thereby respectively uncovering or covering the compartment with the distal sheath 1024. The proximal end of the inner shaft 1026 is affixed to an outer frame 1030 of the operating handle 1020, and the proximal end of the outer shaft 1022 is affixed to a carriage assembly 1040 of the operating handle that is slidable along a longitudinal axis of the frame, such that a user can selectively slide the outer shaft relative to the inner shaft by sliding the carriage assembly relative to the frame.

A hemostasis valve 1028 (shown, for example, in FIG. 14) includes an internal gasket adapted to create a seal between the inner shaft 1026 and the proximal end of the outer shaft 1022. A gasket adjustment wheel 1042 in the carriage assembly 1040 is adapted to adjust the strength of this seal. For example, the gasket inside the hemostasis valve 1028 may be in the shape of an O-ring located around the inner shaft 1026. When the strength of the seal is insufficient, there may be a gap between the O-ring and the outer surface of the inner shaft 1026. To eliminate this gap, a user can turn the gasket adjustment wheel 1042 to place a compressive force on the O-ring in the longitudinal direction of the inner shaft 1026, thereby compressing the O-ring longitudinally and expanding the O-ring radially. The radially expanded O-ring can fill the gap between the O-ring and the outer surface of the inner shaft 1026, thereby creating a liquid-proof seal therebetween.

Figure 15:
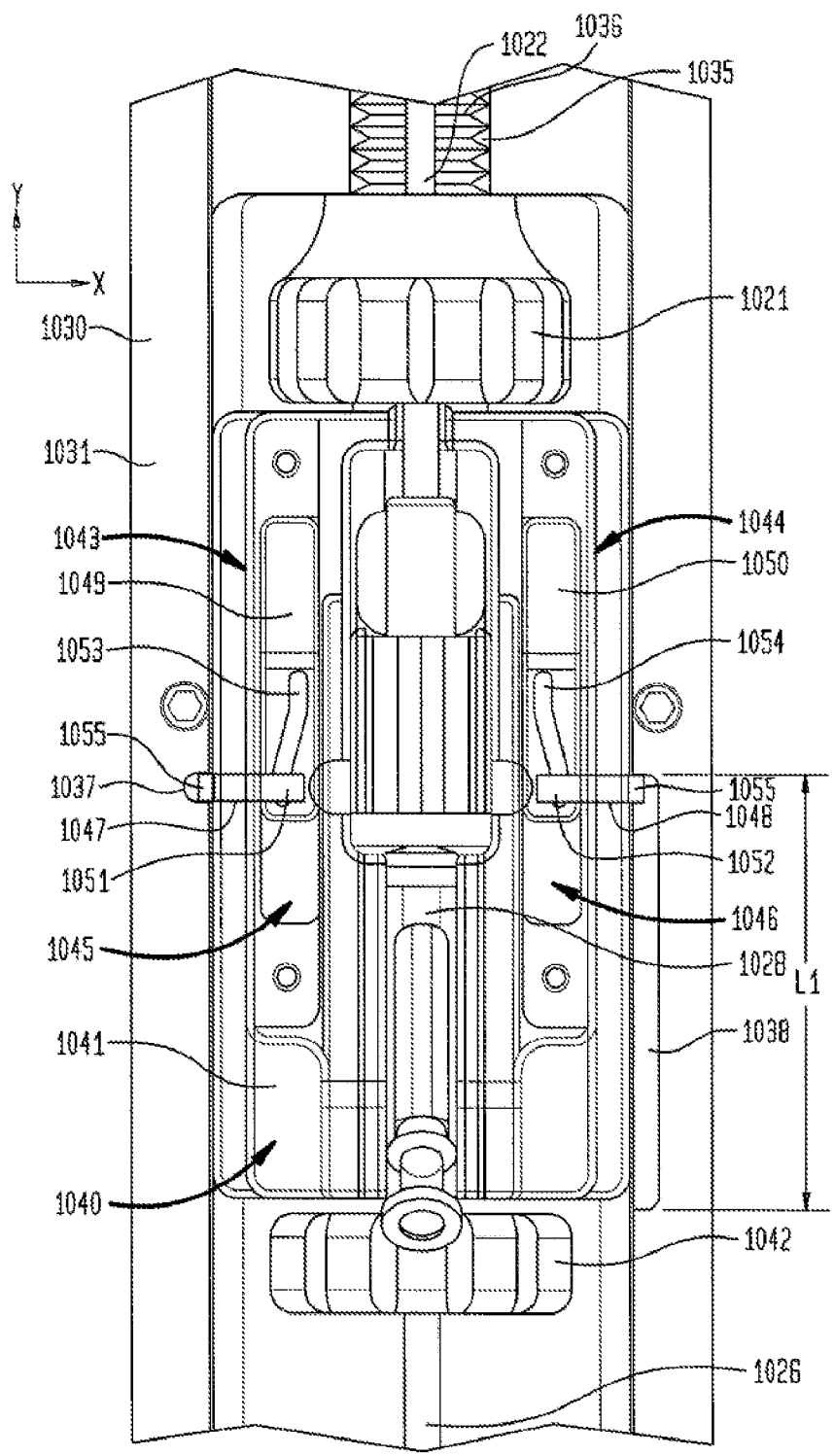
FIG. 15 is an enlarged bottom plan view of the portion of the handle shown in FIG. 14, shown with a transparent carriage assembly.

The frame 1030 includes a pair of side rails 1031 joined at the proximal end 1012 by a proximal end member 1032 and joined at the distal end by a distal end member 1033. Collectively, the side rails 1031, the end member 1032, and the end member 1033 define an elongated space 1034 in the frame 1030 in which the carriage assembly 1040 may travel. The elongated space 1034 preferably permits the carriage assembly 1040 to travel a distance that is at least as long as the anticipated length of the prosthetic valve to be delivered (e.g., at least about 50 mm), such that the distal sheath 1024 can be fully retracted off of the prosthetic valve. An enlarged bore 1035 in the end member 1033 is sized to freely and slidingly receive a threaded rod 1036 (shown in FIG. 13) extending from the distal end of the carriage assembly 1040, as described below. The enlarged bore 1035 has a smooth interior surface and has an inner diameter slightly larger than the outer diameter of the threaded rod 1036 (a longitudinal cross-section of the threaded rod positioned inside of the enlarged bore is shown in FIG. 15).

The carriage assembly 1040 includes a main body 1041 and the threaded rod 1036 extending distally therefrom along the longitudinal axis of the outer frame 1030. The threaded rod 1036 preferably is longer than the anticipated maximum travel distance of the carriage assembly 1040 within the elongated space 1034 (e.g., at least about 50 mm), such that the threaded rod does not fully withdraw from the enlarged bore 1035 during deployment of the prosthetic valve.

A deployment actuator 1021 is threadedly engaged with the threaded rod 1036. The deployment actuator is positioned in abutting relationship with the end member 1033 of the frame 1030 so that rotation of the actuator in one direction (either clockwise or counterclockwise depending on the orientation of the threads on the threaded rod 1036) causes the threaded rod and the carriage assembly 1040 to move proximally within the elongated space 1034. Rotation of the deployment actuator 1021 in the opposite direction, however, does not cause translational movement of carriage assembly 1040, but rather simply causes the deployment actuator to threadedly advance on the threaded rod 1036 as it moves away from the end member 1033 of the frame 1030. Although the movement of the deployment actuator 1021 away from the end member 1033 of the frame 1030 enables the carriage assembly 1040 to move distally until the deployment actuator again contacts the distal end member 1033 of the frame, such movement is not easily controllable, but rather is subject to the "touch and feel" of the user.

In a variant of the embodiment described above, the deployment actuator 1021 may be longitudinally constrained relative to the frame 1030, for example, by the engagement of an annular rib on the distal end of the deployment actuator with an annular groove in the bore 1035 so that the deployment actuator 1021 may rotate in either direction without moving away from the distal end member 1033 of the frame. Rather than an annular rib and an annular groove, any mechanism may be used for longitudinally fixing the deployment actuator 1021 relative to the distal end 1033 of the frame 1030 so as to permit rotation of the deployment actuator in both directions without translation of same within the space 1034. Such an arrangement would provide a user with the ability to carefully control movement of the carriage assembly 1040 both proximally within the space 1034 during a valve deployment operation, and distally within the space 1034 during a resheathing operation, as described more fully below.

Figure 16:
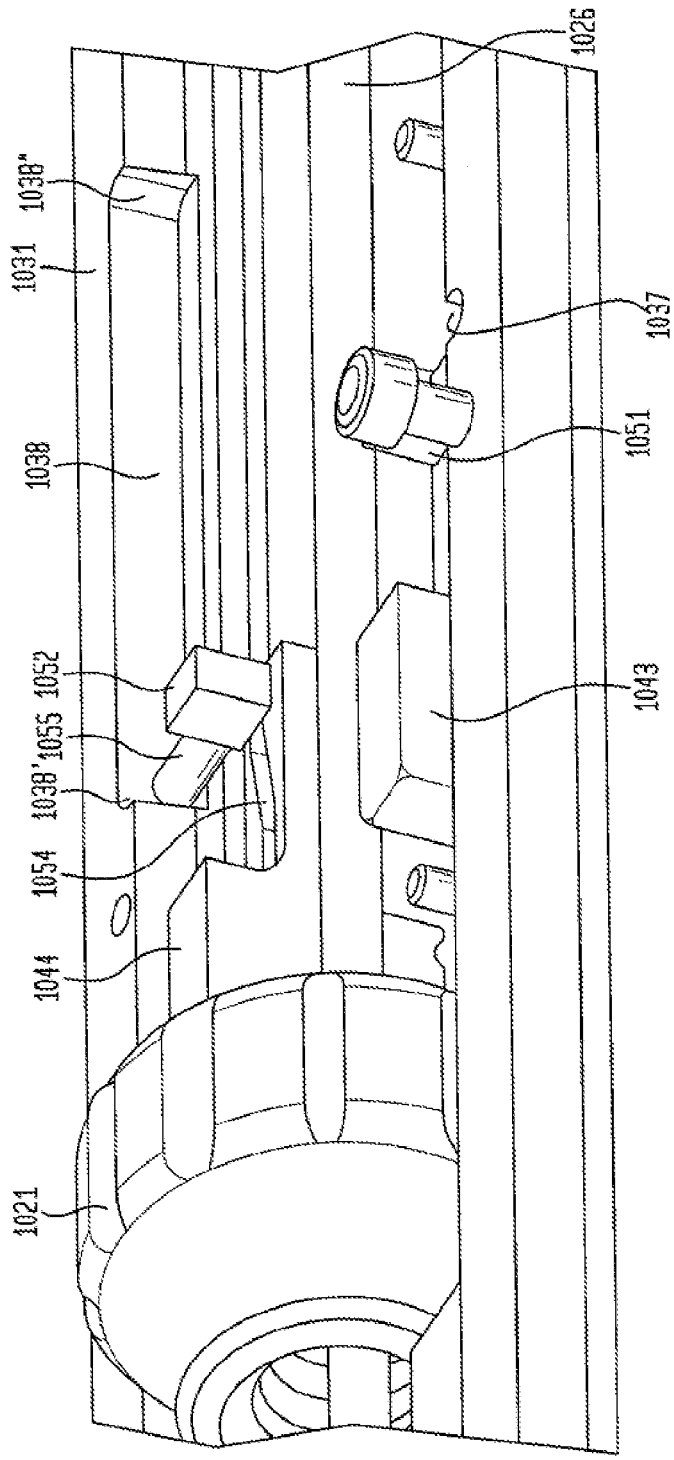
FIG. 16 is an enlarged perspective view of a portion of the handle of FIG. 11, shown without the carriage assembly.
Figure 17:
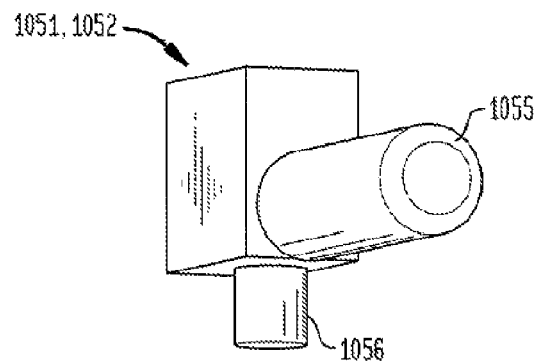
FIG. 17 is an enlarged perspective view of the locking member of the handle shown in FIG. 16.

Referring now to FIGS. 15-17, the carriage assembly 1040 includes a deployment lock 1043 adapted to prevent any movement of the carriage assembly within the frame 1030, thereby preventing a user from accidentally initiating deployment of a prosthetic valve. The deployment lock 1043 includes a control member 1049 that is longitudinally slidable in a slot 1045 between a distal position (shown in FIG. 15) and a proximal position (not shown). The control member 1049 includes a cam slot 1053 disposed in its upper surface, the distal end of the cam slot being spaced farther from the adjacent side rail 1031 than the proximal end thereof. A locking member 1051 includes a downwardly projecting pin 1056 which travels in the cam slot 1053. The locking member 1051 also has a laterally projecting pin 1055 which extends through an aperture 1047 in the main body 1041. With the carriage assembly 1040 in its initial position, the aperture 1047 is aligned with a recess 1037 in the side rail 1031 of the frame 1030. When the control member 1049 is in its distalmost or locked position (shown in FIG. 15), the pin 1056 of the locking member 1051 will be at the proximal end of the cam slot 1053, such that the pin 1055 will extend through the aperture 1047 and into the recess 1037, thus locking the carriage assembly 1040 from any longitudinal movement relative to the frame 1030. Movement of the control member 1049 proximally to an unlocked position causes the pin 1056 of the locking member 1051 to move toward the distal end of the cam slot 1053, thereby moving the locking member laterally inward until the pin 1055 is no longer engaged in the recess 1037. This action thus frees the carriage assembly 1040 for longitudinal movement relative to the frame 1030.

The carriage assembly 1040 also includes a resheathing lock 1044 adapted to limit the longitudinal movement of the carriage assembly within the outer frame 1030, thereby preventing a user from accidentally completing the deployment of a prosthetic valve. The resheathing lock 1044 includes a control member 1050 that is longitudinally slidable in a slot 1046 between a distal position (shown in FIG. 15) and a proximal position (not shown). The control member 1050 includes a cam slot 1054 disposed in its upper surface, the distal end of the cam slot being spaced farther from the adjacent side rail 1031 than the proximal end thereof. A locking member 1052 includes a downwardly projecting pin 1056 which travels in the cam slot 1054. The locking member 1052 also has a laterally projecting pin 1055 which extends through an aperture 1048 in the main body 1041. With the carriage assembly 1040 in its initial position, the aperture 1048 is aligned with the distal end 1038' of a longitudinally extending slot 1038 in the side rail 1031 of the frame 1030. When the control member 1050 is in its distalmost position (shown in FIG. 15), the pin 1056 of the locking member 1052 will be at the proximal end of the cam slot 1054, such that the pin 1055 will extend through the aperture 1048 and into the slot 1038. Such condition will enable the carriage assembly 1040 to move longitudinally within the frame 1030 between an initial position at which the pin 1055 contacts the distal end 1038' of the slot 1038 and a position at which the pin 1055 contacts the proximal end 1038" of the slot 1038. Movement of the control member 1050 proximally causes the pin 1056 of the locking member 1052 to move toward the distal end of the cam slot 1054, thereby moving the locking member laterally inward until the pin 1055 is no longer engaged in the slot 1038. This action thus frees the carriage assembly 1040 for further proximal movement relative to the frame 1030, thereby permitting full deployment of a prosthetic valve from the compartment 1023 of catheter assembly 1016.

The slot 1038 has a length L1 between the distal end 1038' and the proximal end 1038" that is slightly greater than the initial distance that the carriage assembly 1040 may travel while still permitting resheathing of the valve contained in the compartment 1023. More particularly, the length L1 is equal to this initial travel distance plus the diameter of the pin 1055. As a result, when the resheathing lock 1044 is in the locked position, the carriage assembly 1040 can move proximally relative to the frame 1030 only by this amount.

The initial distance that the carriage assembly 1040 can travel before being limited by the proximal end 1038" of the slot 1038 may depend on the structure of the particular prosthetic valve to be deployed. Preferably, the initial travel distance of the carriage assembly 1040 is about 3 mm to about 5 mm less than the crimped valve length. Alternatively, the initial travel distance of the carriage assembly 1040 may be about 40 mm to about 45 mm, which is about 80% to about 90% of the length of an exemplary 50 mm valve. In other arrangements, the initial distance that the carriage assembly 1040 can travel and/or the length of the slot 1038 can be determined as a percentage of the length of the prosthetic valve and/or of the compartment 1023, including, for example, 50%, 60%, 70%, 75%, 85%, or 95%.

The operation of the delivery device 1010 to deploy a prosthetic valve will now be described. To load the delivery device 1010 with a collapsible prosthetic valve, a user can retract the distal sheath 1024 to expose the compartment 1023, place the valve around the inner shaft 1026, couple the proximal end of the valve to the retainer 1025, compresses or crimp the valve, and slide the distal sheath back over the compartment, which holds the valve in a compressed state. In this starting condition, the handle 1020 will be in an initial state with the carriage assembly 1040 at its distalmost position within the frame 1030, the deployment lock 1043 in its locked position to prevent accidental deployment, and the resheathing lock 1044 in its locked position to prevent full deployment once the deployment lock 1043 has been unlocked.

To use the operating handle 1020 to deploy a prosthetic valve that has been compressed and inserted in the compartment 1023 and covered by the distal sheath 1024, a user will initially move the deployment lock 1043 to its unlocked position, thereby freeing the carriage assembly 1040 for longitudinal movement. The user can then rotate the deployment actuator 1021, causing the carriage assembly 1040 to slide proximally within the elongated space 1034 in frame 1030. Because the distal sheath 1024 is affixed to the outer shaft 1022, which in turn is affixed to the carriage assembly 1040, and because the inner shaft 1026 is affixed to the frame 1030, sliding the carriage assembly proximally relative to the frame will retract the distal sheath proximally from the compartment 1023, thereby exposing and initiating deployment of the valve located therein.

It will be appreciated that the user can initiate the deployment process without use of the deployment actuator 1021 by simply grasping the carriage assembly 1040 and pulling same proximally within the frame 1030. Such action requires significant pulling force in order to overcome the frictional forces acting on the outer shaft 1022 and the distal sheath 1024. For that reason, the use of the deployment actuator 1021 to retract the distal sheath 1024 is preferred since such use provides the user with a mechanical advantage to overcome the aforementioned frictional forces, thereby providing the user with much greater control of the deployment process.

In any event, since the resheathing lock 1044 is in the locked position, movement of the carriage assembly 1040 proximally may continue only until the pin 1055 of the locking member 1052 contacts the proximal end 1038" of the slot 1038. At this point, the distal sheath 1024 will not be fully withdrawn from the compartment 1023, and the prosthetic valve will not be fully deployed.

When the deployment procedure has reached this juncture, the user can evaluate the position of the valve and determine whether the annulus end of the valve is properly aligned relative to the patient's aortic annulus. If repositioning is desired, the user may resheath the valve by sliding the carriage assembly 1040 distally within the frame 1030, thereby moving the distal sheath 1024 distally over the compartment 1023 and the partially deployed valve and recollapsing the expanded part of the stent portion of the valve. This may be accomplished by rotating the deployment actuator 1021 to advance it proximally on the threaded rod 1036 and simply pushing the carriage assembly 1040 in the distal direction or, in the variant embodiment in which the deployment actuator 1021 is longitudinally fixed relative to the distal end member 1033 of the frame 1030, by rotating the deployment actuator in the direction opposite that used for deployment. Such rotation will cause the threaded rod 1036 to progress distally through the deployment actuator 1021 until the carriage assembly 1040 has reached the starting condition shown in FIG. 15. With the valve resheathed, the user can reposition the catheter assembly 1016 and commence the deployment procedure once again.

Once the valve has been properly positioned relative to the aortic annulus, the user may complete the deployment process. To do so, the user slides the resheathing lock 1044 from the locked position to the unlocked position, thereby retracting the pin 1055 of locking member 1052 so that the carriage assembly 1040 is free to continue its movement proximally within the frame 1030. The user can complete the deployment of the valve by continuing to slide the carriage assembly 1040 proximally, for example, by rotating the deployment actuator 1021. When the valve has been unsheathed, the stent portion of the valve self-expands and disengages from the retainer 1025, thereby releasing the valve from the catheter assembly 1016.

Figure 18:
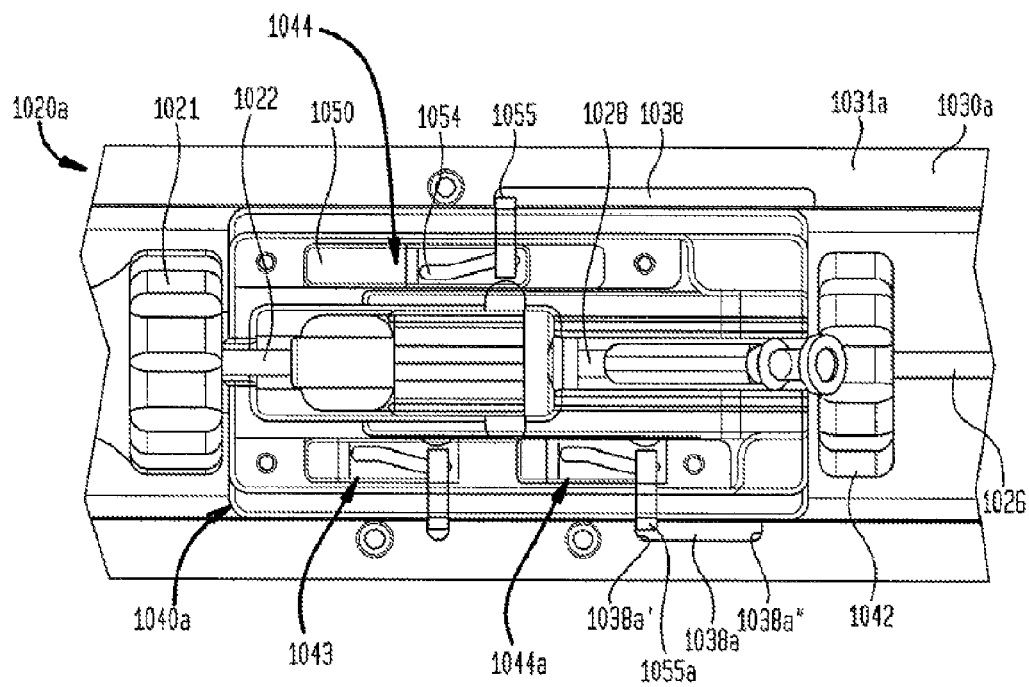
FIG. 18 is an enlarged bottom plan view of a portion of a handle in accordance with another embodiment of the present invention, suitable for use with the transfemoral catheter assembly of FIG. 11.

Referring now to FIG. 18, a portion of an operating handle 1020a in accordance with another embodiment of the invention is shown. The operating handle 1020a is suitable for use with the catheter assembly 1016 described above with reference to FIG. 11. The operating handle 1020a is similar to the operating handle 1020 described above, but differs in that it includes a second resheathing lock 1044a in addition to the first resheathing lock 1044. Hence, the operating handle 1020a is capable of limiting the proximal movement of the carriage assembly 1040a at two separate locations, rather than at a single location. The carriage assembly 1040a is similar to the carriage assembly 1040 shown in FIGS. 11-15, except for the addition of the second resheathing lock 1044a.

The frame 1030a of the operating handle 1020a is similar to the frame 1030 shown in FIGS. 11, 12, and 14-16, except that the side rail on the side opposite resheathing lock 1044 includes a second resheathing slot 1038a. The slot 1038a has a length between its distal end 1038a' and its proximal end 1038a" that is slightly greater than an initial distance that the carriage assembly 1040a may travel to effect a partial deployment of the prosthetic valve. More particularly, the length of the slot 1038a is equal to this initial travel distance plus the diameter of the pin 1055a in the second resheathing lock 1044a. As a result, when the second resheathing lock 1044a is in the locked position, the carriage assembly 1040a can move proximally relative to the frame 1030a only by this amount. Preferably, this initial travel distance of the carriage assembly 1040a is about 25 mm, or about half of the length of a conventional prosthetic aortic valve. In other arrangements, this initial travel distance may be about 40% to about 60% of the length of a conventional prosthetic aortic valve.

The valve deployment process using the operating handle 1020a is similar to the deployment process described above in connection with the operating handle 1020, except for the use of the second resheathing lock 1044a. Thus, to use the operating handle 1020a to deploy a prosthetic valve from compartment 1023 of catheter assembly 1016, the user can first move the deployment lock 1043 to an unlocked position, thereby freeing carriage assembly 1040a for proximal movement relative to the frame 1030a. With the deployment lock 1043 in the unlocked position, the user can rotate the deployment actuator 1021 to move the carriage assembly 1016 proximally until the lateral pin 1055a of resheathing lock 1044a contacts the proximal end 1038a" of the second resheathing slot 1038a.

At this stage of deployment, while the second resheathing lock 1044a is in the locked position, the user can decide to resheath and reposition the valve. At about the halfway-unsheathed position, the valve may be partially functioning, such that the user can assess the valve position and decide whether to continue deployment or to resheath and reposition the valve. If the position of the valve appears to be acceptable, the user can continue to the next stage of deployment by moving the second resheathing lock 1044a to the unlocked position, freeing the carriage assembly 1040a for further proximal movement within the frame 1030a.

With the second resheathing lock 1044a unlocked, the user can continue to rotate the deployment actuator 1021 to further move the carriage assembly 1040a proximally. However, since the resheathing lock 1044 is in the locked position, the proximal movement of the carriage assembly 1040a may continue only until the pin 1055 of the locking member 1052 contacts the proximal end 1038" of the slot 1038. At this point, the distal sheath 1024 will not be fully withdrawn from the compartment 1023, and the prosthetic valve will still not be fully deployed. Once again, the user may evaluate the position of the valve and determine whether repositioning is necessary. If repositioning is desired, the user may resheath the valve by sliding the carriage assembly 1040a distally within the frame 1030a in the manner described above. On the other hand, if the valve position is acceptable, the user may unlock the resheathing lock 1044 and complete the deployment of the valve by continuing to slide the carriage assembly 1040a proximally, such as by rotating the deployment actuator 1021.

Figure 19:
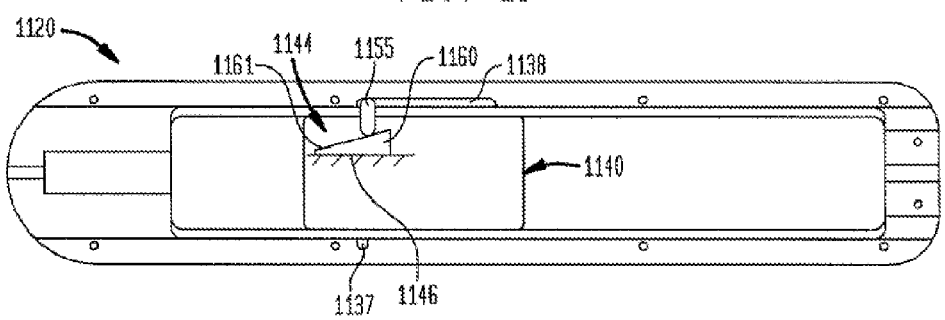
FIG. 19 is a diagrammatic top plan view of another embodiment of a handle suitable for use with the transfemoral catheter assembly of FIG. 11.

Referring now to FIG. 19, an operating handle 1120 in accordance with another embodiment of the invention is shown. The operating handle 1120 is suitable for use with the catheter assembly 1016 described above with reference to FIG. 11. The operating handle 1120 is similar to the operating handle 1020 described above with reference to FIGS. 11-17, but differs in the structure of the deployment lock and the resheathing lock, although these locks function in substantially the same way as described above.

The operating handle 1120 includes a carriage assembly 1140 having a resheathing lock 1144 that controls the lateral retraction of a locking pin 1155. The resheathing lock 1144 includes a cam member 1160 that is slidably mounted in an elongated slot 1146. The cam member 1160 has a tapered surface 1161, such that when the cam member is slid proximally in the slot 1146, the locking pin 1155 retracts in a lateral direction out of the slot 1138, thereby permitting the carriage assembly 1140 to continue proximally past the limit set by the proximal end of slot 1138 and enabling the valve to be fully deployed.

Although the retraction mechanism for the locking pin 1155 is not shown in FIG. 19, when the resheathing lock 1144 is slid proximally, the locking pin 1155 maintains contact with the tapered surface 1161 of the resheathing lock, thereby pulling the locking pin 1155 out of engagement with the slot 1138. For example, a perpendicularly protruding portion of the locking pin 1155 may travel in a slot (similar to how the pin 1056 travels in the cam slot 1054) that forces the locking pin 1155 to maintain contact with the tapered surface of the resheathing lock 1144. Alternatively, the pin 1155 may be inwardly biased by a spring, such that the pin is pulled out of the slot 1138 by the spring as the cam member 1160 is slid proximally in the slot 1146. Other arrangements for retracting locking pin 1155 will be known to the skilled artisan and may be used herewith.

Although a deployment locking mechanism is not shown in FIG. 19, a deployment lock similar in structure to the resheathing lock 1144 can be included that is capable of engaging and withdrawing a second locking pin into and out of the recess 1137 located in the frame side rail opposite the slot 1138.

Figure 20:
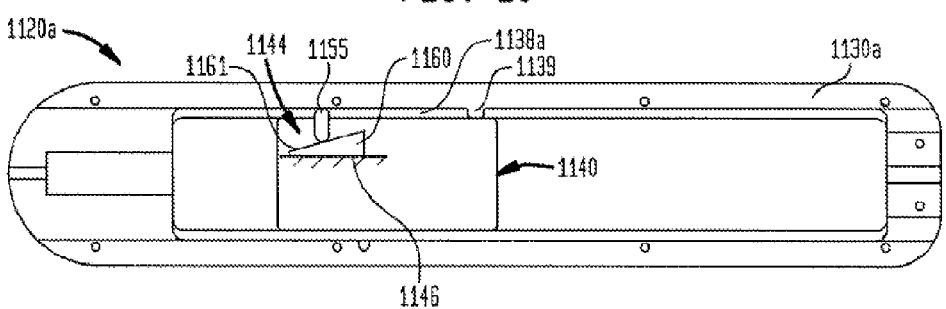
FIG. 20 is a diagrammatic top plan view of a further embodiment of a handle suitable for use with the transfemoral catheter assembly of FIG. 11.

Referring now to FIG. 20, an operating handle 1120a in accordance with yet another embodiment of the invention is shown. The operating handle 1120a is similar to the operating handle 1120 described above, but differs in the structure of the resheathing lock, although the functioning of the resheathing lock is similar to that of the resheathing lock 1044 of operating handle 1020.

Rather than having a resheathing lock mechanism that includes a slot that is closed on both ends, such as the slot 1038 described above in connection with the operating handle 1020, the operating handle 1120a has a frame 1130a that includes a protuberance 1139 that defines the proximal end of a recess 1138a that is open on the distal end. The protuberance 1139 is positioned on the frame 1130a in substantially the same position as the proximal end 1038" of the slot 1038 is positioned in the operating handle 1020.

During staged deployment of a prosthetic valve, when the locking pin 1155 contacts the protuberance 1139, the proximal movement of the carriage assembly 1140 is stopped. While the resheathing lock 1144 is in the locked position (shown in FIG. 20), the valve can be resheathed and repositioned if desired. When it is desired to fully deploy the valve, the user can unlock the resheathing lock 1144 by sliding the cam member 1160 proximally in the slot 1146 to retract the locking pin 1155 from the recess 1138a so that the protuberance 1139 no longer limits the proximal movement of the carriage assembly 1140. The carriage assembly 1140 is thus free to further move proximally and enable the valve to be fully deployed.

Figure 21:
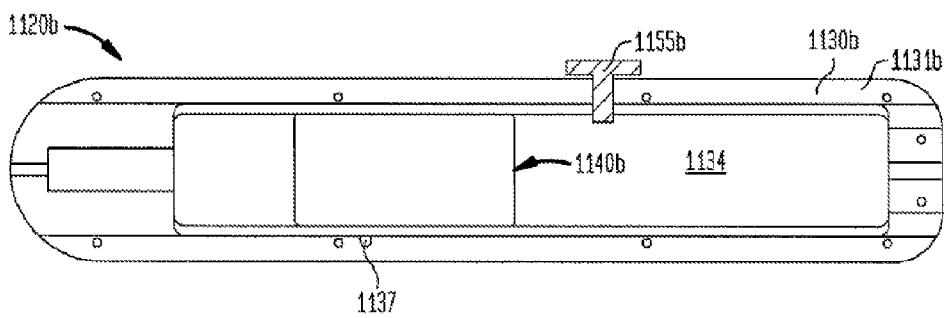
FIG. 21 is a diagrammatic top plan view of yet another embodiment of a handle suitable for use with the transfemoral catheter assembly of FIG. 11.

Referring now to FIG. 21, an operating handle 1120b in accordance with a still further embodiment of the invention is shown. The operating handle 1120b is similar to the operating handles 1120 and 1120a described above, but differs in the structure of the resheathing lock, although the functioning of the resheathing lock is similar to that of the resheathing lock 1044 of the operating handle 1020.

Rather than having a resheathing lock that includes a slot that is closed on both ends, such as the slot 1038 described above in connection with the operating handle 1020, or a recess that is closed on one end, such as the recess 1138a described above in connection with the operating handle 1120a, the operating handle 1120b includes a carriage assembly 1140b and a resheathing lock member 1155b that projects through the side rail 1131*b* of the frame 1130*b* and into the elongated space 1134 so as to obstruct the path of travel of the carriage assembly 1140*b* in the proximal direction. As such, the resheathing lock member 1155*b* defines the initial distance that the carriage assembly 1140*b* may travel before full deployment of the valve occurs. The resheathing lock member 1155*b* may be moved to an unlocked position by retracting the lock member by a sufficient amount that it no longer protrudes into the space 1134. With the resheathing lock member 1155*b* in the unlocked position, the carriage assembly 1140*b* may continue to move proximally, thereby allowing for full deployment of the valve. Optionally, the locking member 1155*b* may be designed to be fully removable from the frame 1130*b* and disposable.

Referring now to FIG. 22, an exemplary transapical delivery device 1210 for a collapsible prosthetic heart valve (or other types of self-expanding collapsible stents) has a catheter assembly 1216 for delivering the heart valve to and deploying the heart valve at a target location, and an operating handle 1220 for controlling deployment of the valve from the catheter assembly. The delivery device 1210 extends from a proximal end 1212 to a distal tip 1214. The catheter assembly 1216 is adapted to receive a collapsible prosthetic heart valve (not shown) in a compartment 1223 defined around a tubular support shaft 1221 and covered by a distal sheath 1224.

The support shaft 1221 extends between a pair of spaced retainers 1225 and 1227 affixed thereto and defining the ends of the compartment 1223. A collapsible prosthetic valve may be assembled around the support shaft 1221 and between the retainers 1225 and 1227 in the compartment 1223.

The distal sheath 1224 surrounds the support shaft 1221 and is slidable relative to the support shaft such that it can selectively cover or uncover the compartment 1223. The distal sheath 1224 is affixed at its distal end to the distal tip 1214, and its proximal end 1229 abuts the retainer 1227 when the distal sheath is fully covering the compartment 1223, as shown in FIG. 22. The proximal end 1229 of the distal sheath 1224 is spaced apart from the retainer 1227 when the compartment 1223 is at least partially uncovered.

The delivery device further includes an outer shaft 1222, the proximal end of which is connected to the operating handle 1220, and the distal end of which is connected to the retainer 1227. An inner shaft 1226 extends through the operating handle 1220 and the support shaft 1221 to the distal tip 1214. The connection of the distal sheath 1224 to the distal tip 1214 thus enables the inner shaft 1226 to control the movement of the distal sheath both proximally and distally.

The operating handle 1220 is adapted to control deployment of a prosthetic valve located in the compartment 1223 by permitting a user to selectively slide the inner shaft 1226 and the attached distal sheath 1224 distally or proximally relative to the support shaft 1221, thereby respectively uncovering or covering the compartment with the distal sheath. The proximal end of the outer shaft 1222 is affixed to an outer frame 1230 of the operating handle 1220, and the proximal end of the inner shaft 1226 is affixed to a carriage assembly 1240 of the operating handle that is slidable along a longitudinal axis of the frame, such that a user can selectively slide the inner shaft relative to the outer shaft by sliding the carriage assembly relative to the frame. A hemostasis valve 1228 provides an internal gasket adapted to create a seal between the inner shaft 1226 and the proximal end of the outer shaft 1222. The strength of this seal may be adjusted by a gasket adjustment wheel 1242 that functions in substantially the same manner as the adjustment wheel 1042 described above.

The frame 1230 includes a pair of side rails 1231 joined at the proximal end 1212 by an end member 1232 and at the distal end by an end member 1233. Collectively, the side rails 1231, the end member 1232, and the end member 1233 define an elongated space 1234 in the frame 1230 in which the carriage assembly 1240 may travel.

The carriage assembly 1240 is shown in FIG. 22 without a threaded rod or a deployment actuator, such as described above in connection with the operating handle 1020. However, it will be appreciated that the operating handle 1220 may have the same components as are provided at the distal end member 1033 of operating handle 1020, but these components would be arranged at the proximal end 1212 of the handle 1220. That is, the proximal end member 1232 of the operating handle 1220 may have an enlarged bore sized to slidingly receive a threaded rod extending from the proximal end of the carriage assembly 1240. A deployment actuator may be threadedly assembled on the threaded rod between the carriage assembly 1240 and the proximal end member 1232 of the frame 1230 such that rotation of the deployment actuator controllably urges the carriage assembly distally within the elongated space 1234. Moreover, the deployment actuator may be longitudinally fixed relative to the proximal end member 1232 such that rotation of the deployment actuator in the opposite direction causes the carriage assembly 1240 to move proximally relative to the frame 1230.

The operating handle 1220 may also include one or more lock mechanisms adapted to prevent accidental partial or full deployment of a prosthetic valve located in the compartment 1223. Thus, as with all of the operating handles described above, the operating handle 1220 may include a deployment lock for preventing a user from accidentally initiating deployment of a valve, as well as a resheathing lock for preventing the user from accidentally completing deployment of the valve. The structures of these lock mechanisms may be similar to the structures of any of the lock mechanisms described above, but modified to limit the movement of the carriage assembly 1240 distally relative to the frame 1230. For example, the lock mechanism may be similar to that included in the operating handle 1120*b* shown in and described with reference to FIG. 21, except that the resheathing lock member 1255 that projects through the side rail 1231 of the frame 1230 and into the elongated space 1234 is located distally of the carriage assembly 1240 (as opposed to proximally as in FIG. 21). Thus, the resheathing lock member 1255 defines the initial distance which the carriage assembly 1240 may travel in the distal direction before full deployment of the valve occurs.

The operation of the operating handle 1220 to deploy a prosthetic valve from the compartment 1223 is similar to the operation of the operating handle 1020 described above with reference to FIGS. 11-17, except that the operating handle 1220, as shown, does not include a deployment actuator to provide the user with mechanical advantage. After moving the deployment lock, if any, to an unlocked condition, the user can grasp the carriage assembly 1240 and push the same distally within the elongated space 1234 in the frame 1230, which thereby pushes the distal sheath 1224 distally relative to the compartment 1223 and exposes and initiates deployment of the valve located therein.

Since the resheathing lock member 1255 is in the locked position, movement of the carriage assembly 1240 distally may continue only until the distal end of the carriage assembly contacts the lock member. At this juncture, the distal sheath 1224 will not fully uncover the compartment 1223, and the prosthetic valve will not be fully deployed. Therefore, if the user desires to resheath and reposition the valve before full deployment, the user can do so by grasping the carriage assembly 1240 and sliding it proximally within the frame 1230 until the carriage assembly contacts the proximal end 1232 of the frame. Once the valve has been properly positioned, the deployment operation may be completed by withdrawing the resheathing lock member 1255 to the unlocked position and moving the carriage assembly 1240 further distally until the valve is fully deployed.

Although the operating handles have been described herein as having one or two resheathing locks, any number of resheathing locks may be used, with or without a deployment lock, resulting in any number of stages in the deployment process. For example, there may be three, four, five, six or more resheathing locks, which thus enable the deployment procedure to be controlled incrementally.

More particularly, if a user desires, for example, a two-stage deployment process, a single resheathing lock may be used, resulting in an unsheathing of perhaps about 80% to about 90% of the valve in a first deployment stage, followed by an unsheathing of the remaining about 10% to about 20% of the valve in a second deployment stage.

If the user desires a three-stage deployment process, on the other hand, a single resheathing lock may be used with a deployment lock, resulting in a first deployment stage in which no deployment can occur, a second deployment stage in which, for example, about 80% to about 90% of the valve is unsheathed, and a third deployment stage in which the remaining about 10% to about 20% of the valve is unsheathed.

Still further, if the user desires a four-stage deployment process, two resheathing locks may be used with a deployment lock, resulting in a first deployment stage in which no deployment can occur, a second deployment stage in which, for example, about 50% of the valve is unsheathed, a third deployment stage in which, for example, about 80% to about 90% of the valve is unsheathed, and a fourth deployment stage in which the remaining about 10% to about 20% of the valve is unsheathed. This last process may be modified to a three-stage deployment process by omitting the deployment lock while keeping the two resheathing locks.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
    a collapsible and expandable stent having a proximal end, a distal end, an annulus section adjacent the proximal end, an aortic section adjacent the distal end, and a plurality of cells having a closed shape disposed continuously in annular rows around a circumference of the stent from the proximal end to the distal end, each of the cells being formed by a plurality of struts and having a first end pointing toward the distal end of the stent and a second end pointing toward the proximal end of the stent, the first end of each cell in a group of cells in the annulus section being connected directly to the second end of an adjacent cell, the annulus section having a first expanded cross-section and the aortic section having a second expanded cross-section larger than the first expanded cross-section;
    the stent including a plurality of commissure features disposed in the annulus section, each of the commissure features being connected to the first end of one cell in one annular row and the second end of another cell adjacent the one annular row, and each of the commissure features being disposed closer to the proximal end than the another cell; and
    a collapsible and expandable valve assembly disposed entirely within the annulus section between the proximal end of the stent and the plurality of commissure features, the valve assembly including a plurality of leaflets connected to the plurality of commissure features;
    the plurality of commissure features being spaced from the distal end of the stent by a selected distance such that the prosthetic valve can be partially deployed from a delivery device at a target site by withdrawing a portion of a sheath of the delivery device from around the prosthetic valve, and the valve assembly can function as intended while the distal end of the stent is held within the sheath of the delivery device in a manner that enables resheathing.

2. The prosthetic heart valve of claim 1, wherein the selected distance is about two-thirds of the length of the stent from the proximal end to the distal end.

3. The prosthetic heart valve of claim 1, wherein the plurality of leaflets have an open condition in which the leaflets are spaced apart from one another to define a flow passageway through the stent, and a closed condition in which the leaflets coapt to occlude the flow passageway, the leaflets being disposed completely within the annulus section in both the open and closed conditions.

4. The prosthetic heart valve of claim 1, wherein the valve assembly further comprises a cuff disposed only in the annulus section.

5. The prosthetic heart valve of claim 4, wherein the cuff is disposed on a lumenal surface of the annulus section.

6. The prosthetic heart valve of claim 4, wherein the cuff is disposed on an ablumenal surface of the annulus section.

7. The prosthetic heart valve of claim 1, wherein the plurality of leaflets are coupled to the stent.

8. The prosthetic heart valve of claim 1, wherein the plurality of leaflets includes three leaflets.

9. The prosthetic heart valve of claim 1, wherein the plurality of leaflets includes two leaflets.

10. The prosthetic heart valve of claim 1, further comprising sutures connecting the plurality of leaflets to the plurality of commissure features.

11. A system, comprising:
    a delivery device having a valve-receiving compartment and a sheath slidable relative to the valve-receiving compartment; and
    the prosthetic heart valve of claim 1;
    wherein the sheath is capable of being withdrawn from around the prosthetic valve to expose the commissure features, wherein the valve assembly is free to operate as intended in a portion of the stent not retained by the sheath.

12. A prosthetic heart valve, comprising:

a collapsible and expandable stent having a proximal end, a distal end, an annulus section adjacent the proximal end, an aortic section adjacent the distal end, a transition section between the aortic section and the annulus section, and a plurality of cells having a closed shape disposed continuously in annular rows around a circumference of the stent from the proximal end to the distal end, each of the cells being formed by a plurality of struts and having a first end pointing toward the distal end of the stent and a second end pointing toward the proximal end of the stent, the first end of each cell in a group of cells in the annulus section being connected directly to the second end of an adjacent cell, the annulus section having a first expanded cross-section, the aortic section having a second expanded cross-section larger than the first expanded cross-section, and the transition section having an expanded cross-section which transitions from the first expanded cross-section to the second expanded cross-section;

the stent including a plurality of commissure features disposed at a juncture between the annulus section and the transition section, each of the commissure features being connected to the first end of one cell in one annular row and the second end of another cell adjacent the one annular row, and each of the commissure features being disposed closer to the proximal end than the another cell; and a collapsible and expandable valve assembly disposed entirely within the annulus section between the proximal end of the stent and the plurality of commissure features, the valve assembly including a plurality of leaflets connected to the plurality of commissure features;

the plurality of commissure features being spaced from the distal end of the stent by a selected distance such that the prosthetic valve can be partially deployed from a delivery device at a target site by withdrawing a portion of a sheath of the delivery device from around the prosthetic valve, and the valve assembly can function as intended while the distal end of the stent is held within the sheath of the delivery device in a manner that enables resheathing.

13. A system, comprising:

a delivery device having a valve-receiving compartment and a sheath slidable relative to the valve-receiving compartment; and the prosthetic heart valve of claim 12;

wherein the sheath is movable from a first configuration in which the sheath is partially withdrawn from around the prosthetic valve to expose the commissure features so that the valve assembly is free to operate as intended in a portion of the stent not retained by the sheath, and a second configuration in which the sheath substantially completely covers the stent and the valve assembly is incapable of operating as intended.

14. A prosthetic heart valve, comprising:

a collapsible and expandable stent having a proximal end, a distal end, an annulus section adjacent the proximal end, an aortic section adjacent the distal end, and a plurality of cells having a closed shape disposed continuously in annular rows around a circumference of the stent from the proximal end to the distal end, each of the cells being formed by a plurality of struts and having a first end pointing toward the distal end of the stent and a second end pointing toward the proximal end of the stent, the first end of each cell in a group of cells in the annulus section being connected directly to the second end of an adjacent cell, the annulus section having a first expanded cross-section and an unconstrained shape and the aortic section having a second expanded cross-section larger than the first expanded cross-section;

the stent including a plurality of commissure features disposed in the annulus section, each of the commissure features being connected to the first end of one cell in one annular row and the second end of another cell adjacent the one annular row, and each of the commissure features being disposed closer to the proximal end than the another cell; and a collapsible and expandable valve assembly disposed entirely within the annulus section between the proximal end of the stent and the plurality of commissure features, the valve assembly including a plurality of leaflets connected to the plurality of commissure features, the plurality of leaflets having an open condition in which the leaflets are spread apart from one another to define a flow passageway through the stent, and a closed condition in which the leaflets form coaptation sections to occlude the flow passageway, the coaptation sections occluding the flow passageway both when the annulus section has the unconstrained shape and when the annulus section is distorted from the unconstrained shape.

15. The prosthetic heart valve of claim 14, wherein, in the closed condition, the coaptation sections are oriented substantially parallel to a longitudinal axis of the stent.

16. The prosthetic heart valve of claim 15, wherein each coaptation section has a length in a direction from a free-edge of a leaflet toward the stent, the length being between about 1 mm and about 5 mm.

17. The prosthetic heart valve of claim 15, wherein, in the closed condition, each of the plurality of leaflets forms a belly contour before converging at the coaptation section.

18. The prosthetic heart valve of claim 15, wherein, in the closed condition, each of the plurality of leaflets forms a flat belly before converging at the coaptation section.

19. A method of deploying a prosthetic heart valve at a target site, the method comprising:

introducing a delivery device to the target site, the delivery device housing a prosthetic heart valve in a collapsed condition and having an outer sheath surrounding the prosthetic heart valve, the prosthetic heart valve including a collapsible and expandable stent having a proximal end, a distal end, an annulus section adjacent the proximal end, an aortic section adjacent the distal end, a plurality of cells having a closed shape disposed continuously in annular rows around a circumference of the stent from the proximal end to the distal end, each of the cells being formed by a plurality of struts and having a first end pointing toward the distal end of the stent and a second end pointing toward the proximal end of the stent, the first end of each cell in a group of cells in the annulus section being connected directly to the second end of an adjacent cell, the stent including a plurality of commissure features disposed in the annulus section, each of the commissure features being connected to the first end of one cell in one annular row and the second end of another cell adjacent the one annular row, and each of the commissure features being disposed closer to the proximal end than the another cell, and a collapsible and expandable valve assembly disposed entirely within the annulus section between the proximal end of the stent and the plurality of commissure features;

withdrawing the sheath a first distance to partially deploy the prosthetic heart valve at the target site, the prosthetic heart valve being deployed from the proximal end of the stent toward the distal end of the stent such that the valve assembly is fully deployed at the first distance and can function as intended while the distal end of the stent is held within the sheath of the delivery device; and further withdrawing the sheath so as to fully deploy the prosthetic heart valve.

20. The method of claim 19, wherein partially deploying the prosthetic heart valve includes withdrawing the sheath to uncover only the annulus section of the heart valve and fully deploying the heart valve includes withdrawing the sheath to uncover both the annulus section and the aortic section of the heart valve.

21. The method of claim 19, wherein the valve assembly includes a plurality of leaflets connected to the plurality of commissure features, the plurality of leaflets having an open condition in which the leaflets are spaced apart from one another to define a flow passageway through the stent, and a closed condition in which the leaflets coapt to occlude the flow passageway and the plurality of leaflets can fully coapt when the heart valve is partially deployed at the target site.

22. The method of claim 21, wherein the plurality of leaflets are capable of forming coaptation sections to occlude the flow passageway, the coaptation sections occluding the flow passageway both when the annulus section has an unconstrained shape and when the annulus section is distorted from the unconstrained shape.

23. The method of claim 19, further comprising the step of resheathing the prosthetic heart valve.

24. The method of claim 19, wherein introducing the delivery device to the target site includes introducing the delivery device to a target site in vitro.

25. The method of claim 19, wherein introducing the delivery device to the target site includes introducing the delivery device to a target site in a mammal.

26. The method of claim 19, wherein introducing the delivery device to the target site includes introducing the delivery device to a target site in a human patient.

* * * * *